United States Patent
Goudar et al.

(10) Patent No.: US 11,427,848 B2
(45) Date of Patent: *Aug. 30, 2022

(54) METHODS FOR HARVESTING MAMMALIAN CELL CULTURES

(71) Applicant: Amgen Inc., Thousand Oaks, CA (US)

(72) Inventors: Chetan Goudar, Newbury Park, CA (US); Sean Cole, Ventura, CA (US); Nicole Sabo, Camarillo, CA (US); Henry Lin, Fremont, CA (US); Jonathan Lull, Thousand Oaks, CA (US); Tharmala Tharmalingam, Winnipeg (CA)

(73) Assignee: AMGEN INC., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/537,766

(22) Filed: Nov. 30, 2021

(65) Prior Publication Data

US 2022/0136025 A1    May 5, 2022

Related U.S. Application Data

(63) Continuation of application No. 15/316,147, filed as application No. PCT/US2015/034297 on Jun. 4, 2015.

(60) Provisional application No. 62/007,588, filed on Jun. 4, 2014.

(51) Int. Cl.
| | |
|---|---|
| C12P 21/00 | (2006.01) |
| C12M 3/00 | (2006.01) |
| C12M 1/00 | (2006.01) |
| C12N 5/00 | (2006.01) |
| C12M 1/36 | (2006.01) |
| C07K 16/00 | (2006.01) |
| C12M 1/26 | (2006.01) |

(52) U.S. Cl.
CPC ............ *C12P 21/00* (2013.01); *C07K 16/00* (2013.01); *C12M 29/04* (2013.01); *C12M 29/10* (2013.01); *C12M 29/16* (2013.01); *C12M 33/14* (2013.01); *C12M 41/48* (2013.01); *C12M 47/02* (2013.01); *C12N 5/0018* (2013.01); *C07K 2317/14* (2013.01); *C12N 2510/02* (2013.01); *C12N 2511/00* (2013.01)

(58) Field of Classification Search
None
See application file for complete search history.

(56) References Cited

U.S. PATENT DOCUMENTS

| | | |
|---|---|---|
| 4,695,623 A | 9/1987 | Stabinsky |
| 4,897,471 A | 1/1990 | Stabinsky |
| 4,968,607 A | 11/1990 | Dower et al. |
| 5,075,222 A | 12/1991 | Hannum et al. |
| 5,122,469 A | 6/1992 | Mather et al. |
| 5,149,792 A | 9/1992 | Thomason |
| 5,272,064 A | 12/1993 | Thomason |
| 5,378,612 A | 1/1995 | Nakashima et al. |
| 5,395,760 A | 3/1995 | Smith et al. |
| 5,610,279 A | 3/1997 | Brockhaus et al. |
| 5,721,121 A | 2/1998 | Etcheverry et al. |
| 5,767,064 A | 6/1998 | Sims et al. |
| 5,856,296 A | 1/1999 | Mosley et al. |
| 5,981,713 A | 11/1999 | Colotta et al. |
| 6,015,938 A | 1/2000 | Boyle et al. |
| 6,068,775 A | 5/2000 | Custer et al. |
| 6,096,728 A | 8/2000 | Collins et al. |
| 6,204,363 B1 | 3/2001 | Zsebo et al. |
| 6,235,883 B1 | 5/2001 | Jakobovits et al. |
| 6,271,349 B1 | 8/2001 | Dougall et al. |
| 6,337,072 B1 | 1/2002 | Ford et al. |
| 6,544,424 B1 | 4/2003 | Shevitz |
| 6,936,441 B2 | 8/2005 | Reiter et al. |
| 7,420,183 B2 | 9/2008 | Kaiser et al. |
| 7,422,875 B2 | 9/2008 | Kabanov et al. |
| 8,053,238 B2 | 11/2011 | Jin et al. |
| 2004/0185535 A1 | 9/2004 | Wilson et al. |
| 2008/0206819 A1 | 8/2008 | Tsao et al. |
| 2008/0227136 A1 | 9/2008 | Pla et al. |
| 2011/0151506 A1 | 6/2011 | Calvosa et al. |
| 2013/0303732 A1 | 11/2013 | Hewig, III et al. |

FOREIGN PATENT DOCUMENTS

| | | |
|---|---|---|
| CA | 2890813 A1 | 5/2014 |
| DE | 10 2008 051 574 A1 | 4/2010 |
| EP | 0367566 B1 | 5/1997 |
| EP | 0460846 B1 | 2/2002 |
| WO | WO1994/010308 A1 | 5/1994 |
| WO | WO1994/028391 A1 | 12/1994 |
| WO | WO1997/001633 A1 | 1/1997 |
| WO | 2001/23527 A1 | 4/2001 |
| WO | WO2001/036637 A1 | 5/2001 |
| WO | WO2001/092337 A2 | 12/2001 |

(Continued)

OTHER PUBLICATIONS

Altshuler et al., Continuous hybridoma growth and monoclonal antibody production in hollow fiber reactors-separators, Biotechnology and Bioengineering (1986), 28(5):646-658.
Chrysanthopoulos et al., Metabolomics 1-12 for high-resolution monitoring of the cellular physiological state in cell culture engineering, Metabolic Engineering (2010), 23(3): 212-222.
Godawat et al., End-to-end integrated fully continuous production of recombinant monoclonal antibodies, Journal of Biotechnology (2015), 213:13-19.
Goudar et al., Metabolic flux analysis of CHO cells in perfusion culture by metabolite balancing and 2D [<13>C, <1>H] COSY NMR spectroscopy, Metabolic Engineering (2010), 12(2):138-149.
Huang et al., Maximizing productivity of CHO cell-based fed-batch culture using chemically defined media conditions and typical manufacturing equipment, Biotechnology Progress (2010), 26(5):1400-1410.

(Continued)

*Primary Examiner* — Celine X Qian
(74) *Attorney, Agent, or Firm* — Susan E. Lingenfelter

(57) ABSTRACT

The invention provides methods and materials for culturing mammalian cells and harvesting recombinant protein.

5 Claims, 18 Drawing Sheets

(56) References Cited

FOREIGN PATENT DOCUMENTS

| WO | 2002/29084 A2 | 4/2002 | | |
|---|---|---|---|---|
| WO | 2004/005493 A1 | 1/2004 | | |
| WO | 2004058800 A2 | 7/2004 | | |
| WO | 2005/095578 A1 | 10/2005 | | |
| WO | 2008/006494 A1 | 1/2008 | | |
| WO | 2008/152075 A1 | 12/2008 | | |
| WO | WO2008/154014 A2 | 12/2008 | | |
| WO | WO2008/157247 A1 | 12/2008 | | |
| WO | 2009/023562 A2 | 2/2009 | | |
| WO | 2009/086309 A2 | 7/2009 | | |
| WO | 2010/056584 A1 | 5/2010 | | |
| WO | 2011/014838 A1 | 2/2011 | | |
| WO | WO2012/115874 A1 | 8/2012 | | |
| WO | WO2012/145682 A1 | 10/2012 | | |
| WO | 2012/156356 A1 | 11/2012 | | |
| WO | WO2013/006479 A2 | 1/2013 | | |
| WO | WO2013/040444 A1 | 3/2013 | | |
| WO | WO2013/063298 A1 | 5/2013 | | |
| WO | WO2013/138159 A1 | 9/2013 | | |
| WO | WO2014/022102 A1 | 2/2014 | | |
| WO | WO-2014146933 A1 * | 9/2014 | ............ | C12M 21/14 |

OTHER PUBLICATIONS

Rodriguez et al., High productivity of 1-12 human recombinant beta-interferon from a low-temperature perfusion culture, Journal of Biotechnology (2010), 150(4):509-518.

Spyros et al., Metabolic profiling reveals that time related physiological changes in mammalian cell perfusion cultures are bioreactor scale independent, Metabolic Engineering (2013), 19:1-9.

Ghebeh, et al., Development of an Assay for the Measurement of the Surfactant Pluronic F-68 in Mammalian Cell Culture Medium, Analytical Biochemistry (1998) 262: 39-44.

Brady et al., Molecular Mass Analysis of Antibodies by On-Line SEC-MS, *J Am Soc Mass Spectro* (2008), 19(4):502-509.

Chasin et al., Effect of Gamma Rays at the Dihydrofolate Reductase Locus : Deletions and Inversions, *Som. Cell Molec. Genet.* (1986), 12(6):555-556.

Do et al., Mechanism of BLys Action in B Cell Immunity, *Cytokine Growth Factor Rev.* (2002), 13(1):19-25.

Furey, Scale-Up of a Cell Culture Perfusion Process-A Low-Shear Filtration System that Inhibits Filter-Membrane Fouling, *Gen. Eng. News* (2002), 22(7):62-63.

Graham et al., Characteristics of a Human Cell Line Transformed by DNA from Human Adenovirus Type 5, *J. Gen. Virol.* (1977), 36:59-72.

Hakansson et al., Crystal Structure of the Trimeric α-Helical Coiled-Coil and the Three Lectin Domains of Human Lung Surfactant Protein D, *Structure* (1999), 7:255-264.

Harbury et al., a Switch Between Two-, Three-, and Four-Stranded Coiled Coils in GCN4 Leucine Zipper Mutants, *Science* (1993), 262:1401-1405.

Harbury et al., Crystal Structure of an Isoleucine-Zipper Trimer, *Nature* (1994), 371:80-83.

Kolhekar et al. Peptidylglycine α-Hydroxylating Monooxygenase : Active Site Residues, Disulfide Linages, and a Two-Domain Model of the Catalytic Core,, *Biochemistry* (1997), 36:10901-10909.

Liu et al., Development and Qualification of a Novel Virus Removal Filter for Cell Culture Applications, *Biotechnol. Prog.* (2000), 16(3)425-434.

Lovejoy et al., Crystal Structure of a Synthetic Triple-Stranded α-Helical Bundle, *Science* (1993), 259:1288-1293.

Maisonpierre et al., Angiopoietin-2, a Natural Antagonist for Tie2 that Disrupts in vivo Angiogenesis, *Science* (1997), 277(5322):55-60.

Mather, Culture of Testicular Cells in Hormone-Supplemented Serum-Free Medium, *Annals NY Acad. Sci.* (1982), 38344-68.

Rüegg et al., Sequence of Human Transcript Expressed in T-Lymphocytes and Encoding a Fibrinogen-Like Protein, *Gene* (1995), 160:257-262.

Stettler et al., New Disposable Tubes for Rapid and Precise Biomass Assessment for Suspension Cultures of Mammalian Cells, *Biotechnol. Bioeng.* (2006), 95(6):1228-1233.

Urlaub et al., Isolation of Chinese Hanster Cell Mutants Deficient in Dihydrofolate Reductase Activity, *Proc. Natl. Acad. Sci. USA* (1980) 77:4216-4220.

Voisard et al., Potential of Cell Retention Techniques for Large-Scale High Density Perfusion Culture of Suspended Mammalian Cells, *Biotechnol. Bioeng.* (2003), 82:751-765.

Tordahl and Perroud, Bioprocess Technology Department. KTH Stockholm. Sep. 11, 2009, "Study of a perfusion process of Chinese Hamster Ovary cells by A TF filtration in bioreactor".

Master's Thesis of Philip Perroud "Study of a perfusion process of Chinese Hamster Ovary cells by ATF filtration in bioreactor" KTH Royal Institute of Technology 2009.

Murhammer et al., Bio/Technology. Dec. 1988. vol. 6: pp. 1411-1418 "Scaleup of insect cell cultures: Protective effects of pluronic F-68".

Murhammer et al., Biotechnol Prog, 1990a, vol. 6(5): pp. 391-397 "Sparged animal cell bioreactors: Mechanism of cell damage and pluronic F-68 protection".

Goldblum et al., Biotechnol Prog. 1990, vol. 6: pp. 383-390 "Protective effect of methylcellulose and other polymers on insect cells subjected to laminar shear stress".

Ramirez et al. Biotechnol Bioeng. 1990, vol. 36: pp. 911-920 "The role of the plasma membrane fluidity on the shear sensitivity of hybridomas grown under hydrodynamic stress".

Gardner et al., Biotechnol Bioeng, 1990, vol. 35: pp. 940-947 "Effects of stirring and sparging on cultured hvbridoma cells".

Zhang et al., Biotechnol Bioeng, 1993, vol. 41: pp. 685-692 "A comparison of oxygenation methods of high-density perfusion cultures of animal cells ".

Murakami et al., Kagaku Kogaku Ronbunshu. 1992, vol. 18(4): pp. 463-470 "Protective effects of polymeric additives on cell damage caused by sparging in serum-free suspension culture"; English machine translation.

Spectrum Laboratories, 2012 "Conversion of bioreactors to continuous perfusion using hollow fiber cell separators"; pp. 1-29.

Ma et al. Biotechnol Prog. Jul.-Aug. 2004, vol. 20(4): pp. 1183-1191 "Quantitative studies of cell-bubble interactions and cell damage at different pluronic F-68 and cell concentrations".

Kampala and Ozturk. Cell Culture Technology for Pharmaceutical and Cell-Based Therapies, Chapter 11, 2006 "Optimization of hiqh cell density perfusion bioreactors"; pp. 387-416.

Su, Wei Wen; Encyclopedia of Industrial Biotechnology: Bioprocess. Bioseparation, and Cell Technology, 2009 "Bioreactors, perfusion".

Zhou et al., Encyclopedia of Industrial Biotechnology: Bioprocess, Bioseparation, and Cell Technology, 2009 "Mammalian cell bioreactors ".

Vljayasankaran et al., Encyclopedia of Industrial Biotechnology: Bioprocess. Bioseparation, and Cell Technology, 2010 "Animal cell culture media ".

Murhammer, Encyclopedia of Bioprocess Technology: Fermentation, Biocatalysis, and Bioseparation, 1999. vol. 4: pp. 2019-2024 "Plutonic polyols, cell protection".

Chisti, Tibtech. Oct. 2000, vol. 18: pp. 420-432 "Animal-cell damage in sparged bioreactors".

Hu et al., Cytotechnology, 2011, vol. 63(5): pp. 445-460 "The potential of hydrodynamic damage to animal cells of industrial relevance: Current understanding".

Gigout et al., Biotechnol Bioeng. Aug. 1. 2008, vol. 100(5): pp. 975-987 "The fate of pluronic F-68 in chondrocytes and CHO cells".

Chang et al., Colloids Surf B Biointerfaces, Aug. 1, 2017, vol. 156: pp. 358-365 "Investigation of interfacial properties of pure and mixed poloxamers for surfactant mediated shear protection of mammalian cells".

ROMPP Lexikon Chemie, 10. Auflage, 1999 "Poloxamer".

Katakam, et al., J of Pharma Sciences; *Effect of Surfactants on the Physical Stability of Recombinant Human Growth Hormone*, v 84 #6; pp. 713-716, 1995.

(56) References Cited

OTHER PUBLICATIONS

Michaels al; J Biotech; "Polyvinyl alcohol and polyethylene glycol as protectants against fluid-mechanical injury of freely-suspended animal cells ( CRL 8018)"; 19, 1991, pp. 241-258.
Clincke et al., Very High Density of CHO Cells in Perfusion by ATF or TFF in WAVE Bioreactor™ Part I Effect of the Cell Density on the Process. *Biotechnol Prog*, May 21, 2013, vol. 29, No. 3, pp. 754-767; Abstract; p. 755, left column; p. 756, left column; figure 1 Citation is not enclosed due to copyright restrictions.
Pluronic® F68 Solution 10%. Dec. 31, 2006 Citation is not enclosed due to copyright restrictions. A copy may be obtained from the URL at http://www.sigmaaldrich.com/content/dam/sigmaaldrich/docs/Sigma/Product_Information_Sheet/p59915.pdf.

\* cited by examiner

METHODS FOR HARVESTING MAMMALIAN CELL CULTURES

CROSS-REFERENCE TO RELATED APPLICATIONS

This application is a continuation of U.S. application Ser. No. 15/316,147 filed on Dec. 2, 2016, which is a National Stage application under 35 U.S.C. § 371 of International Application No. PCT/US2015/034297, having an international filing date of Jun. 4, 2015, which claims the benefit of US. Provisional Patent Application No. 62/007,588, filed Jun. 4, 2014, all of which are incorporated herein by reference in their entirety for all purposes.

FIELD OF THE INVENTION

The invention provides method and materials for culturing mammalian cells and harvesting recombinant proteins.

BACKGROUND OF THE INVENTION

As the demand for greater quantities of therapeutic recombinant proteins continues to grow, much effort is being placed on process optimization, particularly methods and strategies for growing, feeding, and maintaining production cell cultures which have a positive impact on cell viability and protein recovery.

Developing manufacturing processes for production of recombinant proteins is a complex endeavor where many variables must be balanced. This is particularly true for upstream processes, where every element of the cell culture process can have a large impact on the later stages of production, particularly harvest and downstream processing.

A typical cell culture undergoes a growth phase, this is a period of exponential growth where cell density is increased. The growth phase is followed by a transition phase when exponential cell growth is slowing and protein production starts to increase. This marks the start of the stationary phase, a production phase, where cell density typically levels off and product titer increases. In batch harvest systems, where the cell culture is maintained for a set number of days followed by harvesting the entire culture all at once, the majority of the product may be produced in the last few days prior to harvest when the cell culture typically has reached its greatest output. While this may result in a single high titer harvest, it is at the expense of a non-productive turnaround time to initiate the next run and the lag time to once again achieve peak production. In a continuous harvest systems, where product containing permeate is collected from the cell culture on a continuous basis throughout the production phase, the cell culture duration is extended, but at the expense of lower product titers and higher volumes of waste cell culture fluid to be dealt with during the harvest and purification stages.

Cell culture and harvest process development is ultimately is an exercise in process optimization, trading variables such as processing speed for product titer and product quality. The challenges include, for example, maintaining cell viability, achieving a workable product titer, and balancing the output from the upstream process with what the harvest and downstream processes can handle.

New process methods that provide even incremental improvements in recombinant protein production and recovery are valuable, given the expense of large scale cell culture processes and the growing demand for greater quantities of and lower costs for biological products. Improvements to cell culture processes that can lead to greater product recovery, thereby reducing the costs associated with manufacturing protein therapeutics are needed. The invention fulfills these needs by providing such methods and materials for extending cell culture duration while increasing protein recovery.

SUMMARY OF THE INVENTION

The invention provides a method for an extended periodic harvest comprising establishing a cell culture by inoculating a bioreactor with mammalian cells expressing a recombinant protein, maintaining the cell culture by perfusing fresh cell culture medium into the bioreactor, passing the cell culture through a filter and collecting a permeate, wherein a null permeate is initially collected until a first predetermined parameter is reached, at which time a harvest permeate is collected for a predetermined time, this is followed by alternately collecting a null permeate until a second predetermined parameter is reached, then collecting a harvest permeate for a predetermined time, wherein the alternating collection of null permeate and harvest permeate continues until the cell culture is terminated.

In one embodiment the predetermined parameter is selected from time, viable cell density, packed cell volume or titer.

In one embodiment the first predetermined parameter is at least 12 hours to 25 days following the establishment of the cell culture. In one embodiment the first predetermined parameter is at least 24 to 72 hours following the establishment of the cell culture. In one embodiment the first predetermined parameter is at least 4 days following the establishment of the cell culture. In one embodiment the first predetermined parameter is at least 5 or more days following the establishment of the cell culture. In one embodiment the first predetermined parameter is at least 25 days following the establishment of the cell culture. In one embodiment the first predetermined parameter is at least 5 to 25 days following the establishment of the cell culture. In one embodiment the first predetermined parameter is at least 10 to 12 days following the establishment of the cell culture.

In one embodiment the second predetermined parameter is at least 12 to 72 hours following the collection of the harvest permeate. In one embodiment the second predetermined parameter is at least 24 to 72 hours following the collection of the harvest permeate. In one embodiment the second predetermined parameter is at least 24 to 48 hours following the collection of the harvest permeate.

In one embodiment in the predetermined time is at least 12 to 72 hours. In one embodiment the predetermined time is at least 24 to 72 hours. In one embodiment the predetermined time is at least 24 to 48 hours.

In one embodiment the null permeate is initially collected for at least 24 hours to 25 days, at which time a harvest permeate is collected for 12 to 72 hours, followed by alternately collecting a null permeate for at least 24 hours to 25 days, then collecting a harvest permeate for 12 to 72 hours.

In one embodiment when the null permeate is collected, the filter is a hollow fiber filter having a pore size or molecular weight cut off (MWCO) that retains the recombinant protein in the bioreactor. In a related embodiment the molecular weight cutoff is 300 kDa or less. In a related embodiment the hollow fiber filter is an ultrafilter.

In one embodiment when the harvest permeate is collected, the filter is a hollow fiber filter having a pore size or molecular weight cut off (MWCO) that does not retain the recombinant protein in the bioreactor. In a related embodiment the molecular weight cutoff is at least 500 kDa. In a related embodiment the hollow fiber filter is a microfilter.

In one embodiment the filter is a single unit filter system. In a related embodiment rein the single unit filter system comprises at least one hollow fiber filter component having a pore size or molecular weight cut off (MWCO) that retains the recombinant protein in the bioreactor and at least one hollow fiber filter component having a pore size or molecular weight cut off (MWCO) that does not retain the recombinant protein in the bioreactor. In a related embodiment the molecular weight cutoff of at least one hollow fiber filter component that retains the recombinant protein in the bioreactor is 300 kDa or less. In a related embodiment the molecular weight cutoff of at least one hollow fiber filter component that does not retain the recombinant protein in the bioreactor is at least 500 kDa. In a related embodiment at least one hollow fiber filter component that retains the recombinant protein in the bioreactor is an ultrafilter and at least one hollow fiber filter component that does not retain the recombinant protein in the bioreactor is a microfilter. In a related embodiment the single unit filter system is contained within a housing. In a related embodiment the single unit filter system further comprises a spacer between at least two of the hollow fiber filter components.

In one embodiment when the null permeate is collected it is drawn from at least one hollow fiber filter component having a pore size or molecular weight cut off (MWCO) that retains the recombinant protein in the bioreactor.

In one embodiment when the harvest permeate is collected, it is drawn from at least one hollow fiber filter component having a pore size or molecular weight cut off (MWCO) that does not retain the recombinant protein in the bioreactor.

In one embodiment when the permeate is collected from a filter that is a hollow fiber filter having a pore size or molecular weight cut off that does not retain the recombinant protein in the bioreactor, the fresh cell culture medium is formulated with or supplemented to achieve at least 5 g/L of a non-ionic block copolymer. In a related embodiment the non-ionic block copolymer is a polyoxypropylene-polyoxyethylene block copolymer. In a related embodiment the non-ionic block copolymer is poloxamer 188.

In one embodiment the above method further comprising taking samples during the cell culture processes, evaluating the samples to quantitatively and/or qualitatively monitor characteristics of the recombinant protein and/or the cell culture process. In a related embodiment the samples are quantitatively and/or qualitatively monitored using process analytical techniques.

In one embodiment the perfusing is continuous perfusion. In one embodiment the rate of perfusion is constant. In one embodiment the perfusing is performed at a rate of less than or equal to 1.0 working volume per day. In one embodiment the perfusing is accomplished by a peristaltic pump, a double diaphragm pump, a low shear pump or alternating tangential flow. In a related embodiment the perfusing is accomplished by alternating tangential flow.

In one embodiment the method above further comprises subjecting the cell culture to a temperature shift wherein the cells are cultured a) at first temperature for a first period of time and b) at second temperature for a second period of time. In a related embodiment the temperature shift occurs at the transition between the growth phase and production phase. In a related embodiment the temperature shift occurs during the production phase. In a related embodiment the temperature shift is in response to a predetermined parameter. In a related embodiment the temperature shift is in response to a predetermined parameter wherein achieving the predetermined parameter is determined using a capacitance based biomass probe.

In one embodiment the cell culture is established by inoculating the bioreactor with at least $0.1 \times 10^6$ viable cells/mL. In a related embodiment the inoculum was grown by means of a perfusion process using alternating tangential flow filtration.

In one embodiment prior to entering the bioreactor, the cell culture medium is treated using nanofiltration, high temperature short time (HTST), or UV in combination with filtration.

In one embodiment the bioreactor is a production bioreactor. In a related embodiment the bioreactor has a capacity of at least 500 L. In a related embodiment the bioreactor has a capacity of at least 500 L to 2000 L. In a related embodiment the bioreactor has a capacity of at least 1000 L to 2000 L.

In one embodiment the cell culture medium is a serum-free cell culture medium. In one embodiment the cell culture medium is a serum-free chemically defined cell culture medium. In one embodiment the cell culture medium is a perfusion cell culture medium.

In one embodiment the mammalian cells are Chinese Hamster Ovary (CHO) cells. In one embodiment the recombinant protein is selected from the group consisting of a human antibody, a humanized antibody, a chimeric antibody, a recombinant fusion protein, or a cytokine.

In one embodiment the recombinant protein is purified from the harvest permeate by one or more of flocculation, precipitation, centrifugation, depth filtration, affinity chromatography, size exclusion chromatography, ion exchange chromatography, mixed mode anion exchange chromatography, hydrophobic interaction chromatography or hydroxyapatite chromatography. In one embodiment the method above further comprises taking samples during the purification process, evaluating the samples to quantitatively and/or qualitatively monitor characteristics of the recombinant protein and the purification process.

In one embodiment the recombinant protein is formulated into a pharmaceutically acceptable formulation. In one embodiment is provided a recombinant protein produced by the above method.

In invention also provides a method for harvesting a recombinant protein comprising establishing a cell culture by inoculating a bioreactor with mammalian cells expressing a recombinant protein, maintaining the cell culture by perfusing the cell culture with fresh cell culture medium formulated or supplemented to achieve a concentration of at least 5 g/L of a non-ionic block copolymer and passing the cell culture through a hollow fiber filter having a pore size or molecular weight cut off (MWCO) that does not retain the recombinant protein in the bioreactor and collecting a permeate containing the recombinant protein.

In one embodiment the molecular weight cutoff is at least 500 kDa. In one embodiment the hollow fiber filter is a microfilter.

The invention also provides a method for harvesting a recombinant protein comprising establishing a cell culture by inoculating a bioreactor with mammalian cells expressing a recombinant protein, maintaining the cell culture by perfusing the cell culture with fresh cell culture media formulated or supplemented to achieve a concentration of at least 1 g/L of a non-ionic block copolymer and passing the cell culture through a hollow fiber filter having a pore size or molecular weight cut off (MWCO) that retains the recombinant protein in the bioreactor, and collecting a permeate; once a predetermined parameter is reached perfusing the cell culture with fresh cell culture medium formulated or supplemented to achieve a concentration of at least 5 g/L of a non-ionic block copolymer and passing the cell culture through a hollow fiber filter having a pore size or molecular weight cut off (MWCO) that does not retain the recombinant protein in the bioreactor and collecting a permeate containing the recombinant protein.

In one embodiment the molecular weight cutoff of the hollow fiber filter having a pore size or molecular weight cut off that retains the recombinant protein in the bioreactor is 300 kDa or less. In one embodiment the hollow fiber filter having a pore size or molecular weight cut off that retains the recombinant protein in the bioreactor is an ultrafilter.

In one embodiment the molecular weight cutoff of the hollow fiber filter having a pore size or molecular weight cut off (MWCO) that does not retain the recombinant protein in the bioreactor is at least 500 kDa. In one embodiment the hollow fiber filter having a pore size or molecular weight cut off (MWCO) that does not retain the recombinant protein in the bioreactor is a microfilter.

In one embodiment the a hollow fiber filter having a pore size or molecular weight cut off that retains the recombinant protein in the bioreactor and the hollow fiber filter having a pore size or molecular weight cut off that does not retain the recombinant protein in the bioreactor are components of a single unit filter system.

In one embodiment the non-ionic block copolymer is a polyoxypropylene-polyoxyethylene block copolymer. In one embodiment the non-ionic block copolymer is poloxamer 188.

In one embodiment the method above further comprises taking samples during the cell culture processes, evaluating the samples to quantitatively and/or qualitatively monitor characteristics of the recombinant protein and/or the cell culture process. In one embodiment the samples to quantitatively and/or qualitatively monitored using process analytical techniques.

In one embodiment the perfusing is continuous perfusion. In one embodiment the rate of perfusion is constant. In one embodiment the perfusing is performed at a rate of less than or equal to 1.0 working volume per day. In one embodiment the perfusing is accomplished by a peristaltic pump, a double diaphragm pump, a low shear pump or alternating tangential flow. In one embodiment the perfusing is accomplished by alternating tangential flow.

In one embodiment the method above further comprises subjecting the cell culture to a temperature shift wherein the cells are cultured a) at first temperature for a first period of time and b) at second temperature for a second period of time. In a related embodiment n the temperature shift occurs at the transition between the growth phase and production phase. In a related embodiment the temperature shift occurs during the production phase. In a related embodiment the temperature shift is in response to a predetermined parameter. In a related embodiment the temperature shift is in response to a predetermined parameter wherein reaching the predetermined parameter is determined using a capacitance based biomass probe.

In one embodiment the cell culture is established by inoculating the bioreactor with at least $0.1 \times 10^6$ viable cells/mL. In one embodiment the inoculum was grown by means of a perfusion process using alternating tangential flow filtration.

In one embodiment prior to entering the bioreactor, the cell culture medium is treated using nanofiltration, high temperature short time (HTST), or UV in combination with filtration.

In one embodiment the bioreactor is a production bioreactor. In one embodiment n the bioreactor has a capacity of at least 500 L. In a related embodiment the bioreactor has a capacity of at least 500 L to 2000 L. In a related embodiment the bioreactor has a capacity of at least 1000 L to 2000 L.

In one embodiment the cell culture medium is a serum-free cell culture medium. In one embodiment the cell culture medium is a serum-free chemically defined cell culture medium. In one embodiment the cell culture medium is a perfusion cell culture medium.

In one embodiment the mammalian cells are Chinese Hamster Ovary (CHO) cells.

In one embodiment the recombinant protein is selected from the group consisting of a human antibody, a humanized antibody, a chimeric antibody, a recombinant fusion protein, or a cytokine.

In one embodiment the recombinant protein is purified from the harvest permeate by one or more of flocculation, precipitation, centrifugation, depth filtration, affinity chromatography, size exclusion chromatography, ion exchange chromatography, mixed mode anion exchange chromatography, hydrophobic interaction chromatography or hydroxyapatite chromatography.

In one embodiment the method above further comprises taking samples during the purification process, evaluating the samples to quantitatively and/or qualitatively monitor characteristics of the recombinant protein and the production process.

In one embodiment the recombinant protein is formulated into a pharmaceutically acceptable formulation.

In one embodiment is provided a recombinant protein produced by the above method.

The invention also provides a single unit filter system comprising two or more hollow fiber filter components of different pore sizes or molecular weight cut offs (MWCO), wherein the hollow fiber filter components are secured to one another in series such that a sterile flow path is maintained between the individual hollow fibers and the hollow fiber filter components of different pore size or molecular weight cut offs are isolated from one another with respect to their hollow shell sides from which the permeate is withdrawn, such that permeate can be removed independently from each respective hollow fiber filter component.

In one embodiment at least one hollow fiber filter component has a pore size or molecular weight cut off that retains the recombinant protein in the bioreactor and at least one hollow fiber filter component has a pore size filter that is a hollow fiber filter having a pore size or molecular weight cut off that does not retain the recombinant protein in the bioreactor. In a related embodiment at least one hollow fiber filter component has a molecular weight cutoff of 300 kDa or less and at least one hollow fiber filter component has a molecular weight cutoff of at least 500 kDa. In a related embodiment at least one hollow fiber filter component is an ultrafilter and at least one hollow fiber filter component is a microfilter. In a related embodiment the single unit filter system is contained within a housing. In one embodiment the single filter unit further comprising a spacer between at least two of the hollow fiber filter components The method also provides a method for culturing cells expressing a recombinant protein comprising establishing a cell culture by inoculating a bioreactor with mammalian cells expressing a recombinant protein, maintaining the cell culture by perfusing fresh cell culture medium into the bioreactor, passing the cell culture through a single unit filter system and collecting a permeate, wherein the single unit filter system is attached to the bioreactor and the cell culture is drawn out of the bioreactor and into the single unit filter system by a single pumping system, wherein the cell culture passes through the lumen side of the hollow fibers of the single unit filter system and back into the bioreactor and a permeate is withdrawn from one or more of the hollow fiber filters components.

In one embodiment the method above further comprise taking samples during the cell culture processes, evaluating the samples to quantitatively and/or qualitatively monitor characteristics of the recombinant protein and/or the cell culture process. In a related process the samples are quantitatively and/or qualitatively monitored by process analytical techniques.

In one embodiment the perfusing is continuous perfusion. In one embodiment the rate of perfusion is constant. In one embodiment the perfusing is performed at a rate of less than or equal to 1.0 working volume per day.

In one embodiment the perfusing is accomplished by a peristaltic pump, a double diaphragm pump, a low shear pump or alternating tangential flow. In one embodiment the perfusing is accomplished by alternating tangential flow.

In one embodiment when the permeate is collected from a hollow fiber filter component that has a pore size or molecular weight cut off that does not retain the recombinant protein in the bioreactor, the fresh cell culture medium is formulated with or supplemented to achieve at least 5 g/L of a non-ionic block copolymer. In a related embodiment the non-ionic block copolymer is a polyoxypropylene-polyoxyethylene block copolymer. In a related embodiment the non-ionic block copolymer is poloxamer 188.

In one embodiment the method above further comprises subjecting the cell culture to a temperature shift wherein the cells are cultured a) at first temperature for a first period of time and b) at second temperature for a second period of time. In one embodiment the temperature shift occurs at the transition between the growth phase and production phase. In a related embodiment the temperature shift occurs during the production phase. In a related embodiment the temperature shift is in response to a predetermined parameter wherein reaching the predetermined parameter is determined using a capacitance based biomass probe.

In one embodiment the cell culture is established by inoculating the bioreactor with at least $0.1 \times 10^6$ viable cells/mL. In a related embodiment the inoculum was grown by means of a perfusion process using alternating tangential flow filtration.

In one embodiment prior to entering the bioreactor, the cell culture medium is treated using nanofiltration, high temperature short time (HTST), or UV in combination with filtration.

In one embodiment the bioreactor is a production bioreactor. In a related embodiment the bioreactor has a capacity of at least 500 L. In a related embodiment the bioreactor has a capacity of at least 500 L to 2000 L. In a related embodiment the bioreactor has a capacity of at least 1000 L to 2000 L.

In one embodiment the cell culture medium is a serum-free cell culture medium. In one embodiment the cell culture medium is a serum-free chemically defined cell culture medium. In one embodiment the cell culture medium is a perfusion cell culture medium.

In one embodiment the mammalian cells are Chinese Hamster Ovary (CHO) cells.

In one embodiment the recombinant protein is selected from the group consisting of a human antibody, a humanized antibody, a chimeric antibody, a recombinant fusion protein, or a cytokine.

In one embodiment the recombinant protein is purified from the harvest permeate by one or more of flocculation, precipitation, centrifugation, depth filtration, affinity chromatography, size exclusion chromatography, ion exchange chromatography, mixed mode anion exchange chromatography, hydrophobic interaction chromatography or hydroxyapatite chromatography In one embodiment the method above further comprising taking samples during the purification process, evaluating the samples to quantitatively and/or qualitatively monitor characteristics of the recombinant protein and the production process.

In one embodiment the recombinant protein is formulated into a pharmaceutically acceptable formulation. In one embodiment is provided a recombinant protein produced the method above.

DETAILED DESCRIPTION OF THE INVENTION

Figure 1:
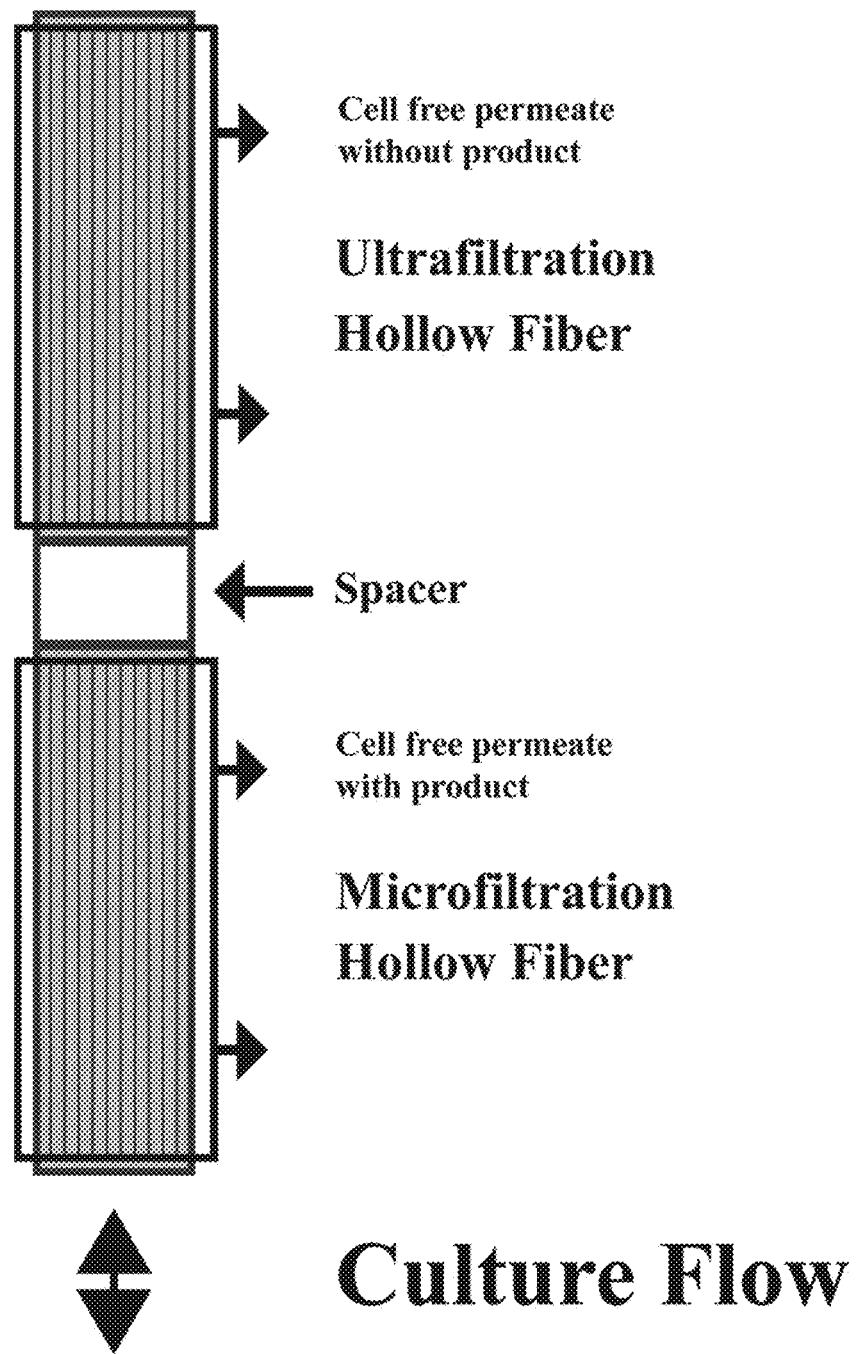
FIG. 1 Schematic of single unit filter system, having a single opening where the cell culture fluid enters and exits through a single opening. Filters can be in any orientation, microfilter hollow fiber followed by ultrafilter hollow fiber is shown.

The invention provides an extended periodic harvest method which offers the advantage of maintaining a continuous cell culture at its peak production while obtaining a high titer permeate. The invention provides a method for extended periodic harvest comprising establishing a cell culture by inoculating a bioreactor with mammalian cells expressing a recombinant protein product, maintaining the cell culture by perfusing fresh cell culture medium into the bioreactor, passing the cell culture through a filter and collecting a permeate, wherein a null permeate is initially collected until a first predetermined parameter is reached, at which time a harvest permeate is collected for a predetermined time, this is followed by alternately collecting a null permeate until a second predetermined parameter is reached, then collecting a harvest permeate for a predetermined time, wherein the alternating collection of the null permeate and harvest permeate continues until the cell culture is terminated.

The predetermined parameters may be reached by achieving some desired characteristic, attribute or performance milestone of the cell culture; such as viable cell density, packed cell volume or titer or a time point. In one embodiment, the predetermined parameter may be reached when the viable cell density is greater than or equal to $1 \times 10^6$ viable cells/ml. In one embodiment, predetermined parameter may be reached when the viable cell density is at least $20 \times 10^6$ viable cells/ml to $30 \times 10^6$ viable cells/ml. In one embodiment, predetermined parameter may be reached when the packed cell volume is less than or equal to 35%. In one embodiment, predetermined parameter may be reached when the packed cell volume is less than or equal to 30%.

The predetermined parameter may be based on a time point. The time point may be measured in hours, days, weeks, or months following a triggering event or action. A triggering event or action may be hours or days in culture, hours or days following an event such as reaching a viable cell density, packed cell volume, titer, inoculating the bioreactor or collecting a harvest permeate. In one embodiment, the predetermined parameter may be reached within 12 hours to 25 days following a triggering event or action. In one embodiment, the predetermined parameter may be reached within 24 to 72 hours following a triggering event or action. In one embodiment, predetermined parameter may be reached within 4 days of the triggering event or action. In one embodiment, predetermined parameter may be reached 5 days or more following the triggering event or action. In one embodiment, predetermined parameter may be reached at least 25 days following the triggering event or action. In one embodiment, the first predetermined parameter may be reached within 5 to 25 days following inoculation of the bioreactor. In one embodiment, the first predetermined parameter may be reached within 10 to 12 days following inoculation of the bioreactor. In one embodiment, a second predetermined parameter may be reached within 12 to 72 hours following the collection of a harvest permeate. In one embodiment, a second predetermined parameter may be reached within 24 to 72 hours following the collection of a harvest permeate. In one embodiment, a second predetermined parameter may be reached within 24 to 48 hours following the collection of a harvest permeate.

Once the predetermined parameter has been reached, a harvest permeate may be collected for a predetermined time. In one embodiment the predetermined time is at least 12 to 72 hours. In one embodiment the predetermined time is 24 to 72 hours. In one embodiment the predetermined time is 24 to 48 hours.

In one embodiment the filter is a single unit filter system. In a related embodiment the single unit filter system comprises at least one hollow fiber filter component having a pore size or molecular weight cut off (MWCO) that retains the recombinant protein in the bioreactor and at least one hollow fiber filter component having a pore size or molecular weight cut off that does not retain the recombinant protein in the bioreactor. In another embodiment the molecular weight cutoff of at least one hollow fiber filter component that retains the recombinant protein in the bioreactor is 300 kDa or less. In another embodiment the molecular weight cutoff of at least one hollow fiber filter component that does not retain the recombinant protein in the bioreactor is at least 500 kDa. In another embodiment at least one hollow fiber filter component that retains the recombinant protein in the bioreactor is an ultrafilter and at least one hollow fiber filter component that does not retain the recombinant protein in the bioreactor is a microfilter. In another embodiment the single unit filter system is contained within a housing. In another embodiment the single unit filter system further comprises a spacer between at least two of the hollow fiber filter components.

In one embodiment when the null permeate is collected using a single unit filter system it is drawn from at least one hollow fiber filter component having a pore size or molecular weight cut off that retains the recombinant protein in the bioreactor. In one embodiment when the harvest permeate is collected using a single unit filter system it is drawn from at least one hollow fiber filter having a pore size or molecular weight cut off that does not retain the recombinant protein in the bioreactor. In one embodiment the permeate is collected from a filter that is a hollow fiber filter having a pore size or molecular weight cut off that does not retain the recombinant protein in the bioreactor, the fresh cell culture medium is formulated with or supplemented to achieve at least 5 g/L of a non-ionic block copolymer. In a related embodiment the non-ionic block copolymer is a polyoxypropylene-polyoxyethylene block copolymer. In another related embodiment the non-ionic block copolymer is poloxamer 188.

The invention also provides a method for harvesting a recombinant protein comprising establishing a cell culture by inoculating a bioreactor with mammalian cells expressing a recombinant protein, maintaining the cell culture by perfusing the cell culture with fresh cell culture medium formulated or supplemented to achieve a concentration of at least 5 g/L of a non-ionic block copolymer and passing the cell culture through a hollow fiber filter having a pore size or molecular weight cut off that does not retain the recombinant protein in the bioreactor and collecting a permeate containing the recombinant protein. In one embodiment the molecular weight cutoff is at least 500 kDa. In one embodiment the hollow fiber filter is a microfilter.

The invention also provides a method for harvesting a recombinant protein comprising establishing a cell culture by inoculating a bioreactor with mammalian cells expressing a recombinant protein, maintaining the cell culture by perfusing the cell culture with fresh cell culture media formulated or supplemented to achieve a concentration of at least 1 g/L of a non-ionic block copolymer and passing the cell culture through a hollow fiber filter having a pore size or molecular weight cut off that retains the recombinant protein in the bioreactor, and collecting a permeate; once a predetermined parameter is reached, perfusing the cell culture with fresh cell culture medium formulated or supplemented to achieve a concentration of at least 5 g/L of a non-ionic block copolymer and passing the cell culture through a hollow fiber filter having a pore size or molecular weight cut off that does not retain the recombinant protein in the bioreactor and collecting a permeate containing the recombinant protein. In one embodiment the molecular weight cutoff of the hollow fiber filter having a pore size or molecular weight cut off that retains the recombinant protein in the bioreactor is 300 kDa or less. In a related embodiment the hollow fiber filter having a pore size or molecular weight cut off that retains the recombinant protein in the bioreactor is an ultrafilter. In one embodiment the molecular weight cutoff of the hollow fiber filter having a pore size or molecular weight cut off that does not retain the recombinant protein in the bioreactor is at least 500 kDa. In a related embodiment the hollow fiber filter having a pore size or molecular weight cut off that does not retain the recombinant protein in the bioreactor is a microfilter. In one embodiment the a hollow fiber filter having a pore size or molecular weight cut off that retains the recombinant protein in the bioreactor and the hollow fiber filter having a pore size or molecular weight cut off that does not retain the recombinant protein in the bioreactor are components of a single unit filter system. In a related embodiment the non-ionic block copolymer is a polyoxypropylene-polyoxyethylene block copolymer. In another related embodiment the non-ionic block copolymer is poloxamer 188.

The invention also provides a single unit filter system comprising two or more hollow fiber filter components of different pore sizes or molecular weight cut offs, wherein the hollow fiber filter components are secured to one another in series such that a sterile flow path is maintained between the individual hollow fibers and the hollow fiber filter components of different pore size or molecular weight cut offs are isolated from one another with respect to their hollow shell sides from which the permeate with withdrawn, such that permeate can be removed independently from each respective hollow fiber filter component. In one embodiment at least one hollow fiber filter component has a pore size or molecular weight cut off that retains the recombinant protein in the bioreactor and at least one hollow fiber filter component has a pore size filter that is a hollow fiber filter having a pore size or molecular weight cut off that does not retain the recombinant protein in the bioreactor. In one embodiment at least one hollow fiber filter component has a molecular weight cutoff of 300 kDa or less and at least one hollow fiber filter component has a molecular weight cutoff of at least 500 kDa. In one embodiment at least one hollow fiber filter component is an ultrafilter and at least one hollow fiber filter component is a microfilter. In one embodiment the single unit filter system is contained within a housing. In one embodiment the single unit filter system further comprising a spacer between at least two of the hollow fiber filter components In a related embodiment the invention provides a method for culturing cells and/or harvesting a recombinant protein comprising expressing a recombinant protein comprising establishing a cell culture by inoculating a bioreactor with mammalian cells expressing a recombinant protein, maintaining the cell culture by perfusing fresh cell culture medium into the bioreactor, passing the cell culture through a single unit filter system and collecting a permeate, wherein the single unit filter system is attached to the bioreactor and the cell culture is drawn out of the bioreactor and into the single unit filter system by a single pumping system, wherein the cell culture passes through the lumen side of the hollow fibers of the single unit filter system and back into the bioreactor and a permeate is withdrawn from one or more of the hollow fiber filters components.

In a related embodiment the methods of the invention further comprise taking samples during the cell culture processes, evaluating the samples to quantitatively and/or qualitatively monitor characteristics of the recombinant protein and/or the cell culture process. In a related embodiment the samples are quantitatively and/or qualitatively monitored using process analytical techniques.

In a related embodiment of the methods of the invention the perfusing is continuous perfusion. In one embodiment the rate of perfusion is constant. In one embodiment the perfusing is performed at a rate of less than or equal to 1.0 working volume per day. In one embodiment the perfusing is accomplished by a peristaltic pump, a double diaphragm pump, a low shear pump or alternating tangential flow. In one embodiment the perfusing is accomplished by alternating tangential flow.

In a related embodiment the methods of the invention further comprise subjecting the cell culture to a temperature shift wherein the cells are cultured a) at first temperature for a first period of time and b) at second temperature for a second period of time. In one embodiment the temperature shift occurs at the transition between the growth phase and production phase. In one embodiment the temperature shift occurs during the production phase. In one embodiment the temperature shift is in response to a predetermined parameter wherein achieving the predetermined parameter is determined using a capacitance based biomass probe. In one embodiment the temperature shift is in response to a predetermined parameter wherein achieving the predetermined parameter is determined using a capacitance based biomass probe.

In a related embodiment of the methods of the invention the cell culture is established by inoculating the bioreactor with at least $0.1 \times 10^6$ viable cells/mL. In one embodiment the inoculum was grown by means of a perfusion process using alternating tangential flow filtration. In one embodiment prior to entering the bioreactor, the cell culture medium is treated using nanofiltration, high temperature short time (HTST), or UV in combination with filtration.

In a related embodiment of the methods of the invention the bioreactor is a production bioreactor. In one embodiment the bioreactor has a capacity of at least 500 L. In one embodiment the bioreactor has a capacity of at least 500 L to 2000 L In one embodiment the bioreactor has a capacity of at least 1000 L to 2000 L.

In a related embodiment of the methods of the invention the cell culture medium is a serum-free chemically defined cell culture medium. In one embodiment the cell culture medium is a perfusion cell culture medium. In one embodiment the mammalian cells are Chinese Hamster Ovary (CHO) cells. In one embodiment the recombinant protein is selected from the group consisting of a human antibody, a humanized antibody, a chimeric antibody, a recombinant fusion protein, or a cytokine.

In a related embodiment of the methods of the invention the recombinant protein is purified from the harvest permeate by one or more of flocculation, precipitation, centrifugation, depth filtration, affinity chromatography, size exclusion chromatography, ion exchange chromatography, mixed mode anion exchange chromatography, hydrophobic interaction chromatography or hydroxyapatite chromatography. In one embodiment the methods of the invention further comprise taking samples during the purification process, evaluating the samples to quantitatively and/or qualitatively monitor characteristics of the recombinant protein and the purification process. In one embodiment the samples are quantitatively and/or qualitatively monitored using process analytical techniques.

In one embodiment the recombinant protein is formulated into a pharmaceutically acceptable formulation.

The invention also provides a recombinant protein produced by any method of the invention.

Cell Culture

By "cell culture" or "culture" is meant the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992).

Mammalian cells may be cultured in suspension or while attached to a solid substrate.

As used herein, the terms "cell culturing medium" (also called "culture medium," "cell culture media," "tissue culture media,") refers to any nutrient solution used for growing cells, e.g., animal or mammalian cells, and which generally provides at least one or more components from the following: an energy source (usually in the form of a carbohydrate such as glucose); one or more of all essential amino acids, and generally the twenty basic amino acids, plus cysteine; vitamins and/or other organic compounds typically required at low concentrations; lipids or free fatty acids; and trace elements, e.g., inorganic compounds or naturally occurring elements that are typically required at very low concentrations, usually in the micromolar range.

The nutrient solution may optionally be supplemented with additional components to optimize growth of cells, such as hormones and other growth factors, such as insulin, transferrin, epidermal growth factor, serum, and the like; salts, such as calcium, magnesium and phosphate, and buffers, e.g., HEPES; nucleosides and bases, such as adenosine, thymidine, hypoxanthine: and protein and tissue hydrolysates, such as hydrolyzed plant or animal protein (peptone or peptone mixtures, which can be obtained from animal byproducts, purified gelatin or plant material); antibiotics, such as gentamycin: polyamines, such as putrescine, spermidine and spermine (see WIPO Publication No. WO 2008/154014) and pyruvate (see U.S. Pat. No. 8,053,238), anti-apoptotic compounds, e.g., MDL 28170, cypermethrin, cyclosporine A. BBMP, Bongkrckic acid, S-15176 difumerate, cyclic pifithrin-a, pifithrin mu, BI-6C9, NSCI, NS3694 or Necrostatin-1 (see WIPO Publication No. WO 2014/022102) depending on the requirements of the cells to be cultured and/or the desired cell culture parameters.

Non-ionic surfactants may also be added to the cell culture medium. Examples of non-ionic surfactants include, but are not limited to, polyvinyl alcohol, polyethylene glycosl, and non-ionic block copolymer surfactants. Also included are alkyl poly(ethylene oxide), copolymers of poly(ethylene oxide) and poly(propylene oxide) (EO-PO block copolymers), poly(vinylpyrrolidone), alkyl polyglucosides (such as sucrose monostearate, lauryl diglucoside, or sorbitan monolaureate, octyl glucoside and decyl maltoside), fatty alcohols (cetyl alcohol or olelyl alcohol), or cocamides (cocamide MEA, cocamide DEA and cocamide TEA).

Also included are block copolymers based on ethylene oxide and propylene oxide, also referred to as polyoxypropylene-polyoxyethylene block copolymers. These molecules are nonionic triblock copolymers having a central hydrophobic chain of polyoxypropylene (poly(propylene oxide)) flanked by two hydrophilic chains of polyoxyethylene (poly(ethylene oxide)). Of particular interest are those having 70 polyoxypropylene units and 30 units of each of the polyoxyethylene chains. In a preferred embodiment the block copolymer is poloxamer 188 (CAS #90003-11-6 with an average molecular weight of 8.4 kd, BASF Chemical, Washington, N.J.) which is sold under various brand names such as PLURONIC® F68, KOLLIPHOR® P-188, LUTROL® F68, and LUTROL® 188.

These polyoxypropylene-polyoxyethylene block copolymers are used to protect cells from bubble-induced death due to sparging and foam in the reactor. As described herein, the level of poloxamer 188 that is typically used in cell culture medium (1 g/L) may not be sufficient to protect cells from high shear forces within an alternating tangential flow (ATF®) perfusion system when cell cultures are 10 exposed to microfiltration. As described herein, adding a polyoxypropylenepolyoxyethylene block copolymer, such as poloxamer 188, at higher concentrations, such as 5 g/L, had a positive impact on cell viability, which enabled longer culture durations under ATF® alternating tangential flow perfusion conditions.

Cell culture media include those that are typically employed in and/or are known for use with any cell culture process, such as, but not limited to, batch, extended batch, fed-batch and/or perfusion or continuous culturing of cells.

A "base" (or batch) cell culture medium or feed medium refers to a cell culture medium that is typically used to initiate a cell culture and is sufficiently complete to support the cell culture.

A "growth" cell culture medium or feed medium refers to a cell culture medium that is typically used in cell cultures during a period of exponential growth, a "growth phase", and is sufficiently complete to support the cell culture during this phase. A growth cell culture medium may also contain selection agents that confer resistance or survival to selectable markers incorporated into the host cell line. Such selection agents include, but are not limited to, geneticin (G4118), neomycin, hygromycin B, puromycin, zeocin, methionine sulfoximine, methotrexate, glutamine-free cell culture medium, cell culture medium lacking glycine, hypoxanthine and thymidine, or thymidine alone.

A "production" cell culture medium or feed medium refers to a cell culture medium that is typically used in cell cultures during the transition when exponential growth is ending and during the subsequent transition and/or production phases when protein production takes over. Such cell culture medium is sufficiently complete to maintain a desired cell density, viability and/or product titer during this phase.

A "perfusion" cell culture medium or feed medium refers to a cell culture medium that is typically used in cell cultures that are maintained by perfusion or continuous culture methods and is sufficiently complete to support the cell culture during this process. Perfusion cell culture medium formulations may be richer or more concentrated than base cell culture medium formulations to accommodate the method used to remove the spent medium. Perfusion cell culture medium can be used during both the growth and production phases.

Cell culture medium components may be completely milled into a powder medium formulation; partially milled with liquid supplements added to the cell culture medium as needed; or added in a completely liquid form to the cell culture.

Cell cultures can be supplemented with concentrated feed medium containing components, such as nutrients and amino acids, which are consumed during the course of the production phase of the cell culture. Concentrated cell culture medium can contain some or all of the nutrients necessary to maintain the cell culture; in particular, concentrated medium can contain nutrients identified as or known to be consumed during the course of the production phase of the cell culture. Concentrated medium may be based on just about any cell culture media formulation.

Concentrated feed medium can contain some or all the components of the cell culture medium at, for example, about 2×, 3×, 4×, 5×, 6×, 7×, 8×, 9×, 10×, 12×, 14×, 16×, 20×, 30×, 50×, 100×, 200×, 400×, 600×, 800×, or even about 1000× of their normal amount.

Cell cultures can also be supplemented with independent concentrated feeds of particular nutrients which may be difficult to formulate or are quickly depleted in cell cultures. Such nutrients may be amino acids such as tyrosine, cysteine and/or cystine (see e.g., WIPO Publication No. 2012/145682). In one embodiment, a concentrated solution of tyrosine is independently fed to a cell culture grown in a cell culture medium containing tyrosine, such that the concentration of tyrosine in the cell culture does not exceed 8 mM. In another embodiment, a concentrated solution of tyrosine and cystine is independently fed to the cell culture being grown in a cell culture medium lacking tyrosine, cystine or cysteine. The independent feeds can begin prior to or at the start of the production phase. The independent feeds can be accomplished by fed batch to the cell culture medium on the same or different days as the concentrated feed medium. The independent feeds can also be perfused on the same or different days as the perfused medium. Such independent feeds can be added to the cell culture medium after one or more days, and can also be added repeatedly during the course of the production phase, as long as tyrosine, cysteine and cystine depletion in the cell culture medium is avoided.

Methods can be employed to continuous feed a mammalian cell culture, such as those that do not employ feedback control (see WIPO Publication No. WO 2013/040444).

Cell culture medium, in certain embodiments, is serum-free and/or free of products or ingredients of animal origin. Cell culture medium, in certain embodiments, is chemically defined, where all of the chemical components are known.

Animal or mammalian cells are cultured in a medium suitable for the particular cells being cultured and which can be determined by the person of skill in the art without undue experimentation. Commercially available media can be utilized and include, but are not limited to, Iscove's Modified Dulbecco's Medium. RPMI 1640, Minimal Essential Medium-alpha. (MEM-alpha). Dulbecco's Modification of Eagle's Medium (DMEM), DME/F12, alpha MEM, Basal Medium Eagle with Earle's BSS, DMEM high Glucose, with Glutamine, DMEM high glucose, without Glutamine, DMEM low Glucose, without Glutamine, DMEM:F12 1:1, with Glutamine, GMEM (Glasgow's MEM), GMEM with glutamine, Grace's Complete Insect Medium, Grace's Insect Medium, without FBS, Ham's F-10, with Glutamine, Ham's F-12, with Glutamine, IMDM with HEPES and Glutamine, IMDM with HEPES and without Glutamine. IP41 Insect Medium, 15 (Leibovitz)(2×), without Glutamine or Phenol Red, 15 (Leibovitz), without Glutamine, McCoy's 5A Modified Medium. Medium 199, MEM Eagle, without Glutamine or Phenol Red (2×), MEM Eagle-Earle's BSS, with glutamine, MEM Eagle-Earle's BSS, without Glutamine, MEM Eagle-Hanks BSS, without Glutamine, NCTC-109, with Glutamine, Richter's CM Medium, with Glutamine, RPMI 1640 with HEPES, Glutamine and/or Penicillin-Streptomycin, RPMI 1640, with Glutamine, RPMI 1640, without Glutamine, Schneider's Insect Medium or any other media known to one skilled in the art, which are formulated for particular cell types. To the foregoing exemplary media can be added supplementary components or ingredients, including optional components, in appropriate concentrations or amounts, as necessary or desired, and as would be known and practiced by those having in the art using routine skill.

Media Treatments

The cell culture medium can treated using methods or devices to sterilize or disinfect media prior to addition to the bioreactor and/or cell culture. In one embodiment, the cell culture media is treated using high temperature short time (HTST) (see, e.g., U.S. Pat. No. 7,420,183). In one embodiment, the cell culture media is treated using UV in combination with filtration (see, e.g., WIPO Publications WO 2008/157247; WO 2012/115874; WO 2013/063298 and WO 2013/138159). In another embodiment, the cell culture media is subjected to nanofiltration (see, e.g., Liu et al., (2000) Biotechnol. Prog. 16:425-434). In another embodiment, the cell culture media is treated with chemicals that inactivate viruses, such as solvents, detergents, psoralen, or beta-propiolactone.

Cells

Cell lines (also referred to as "cells" or "host cells") used in the invention are genetically engineered to express a polypeptide of commercial or scientific interest. Cell lines are typically derived from a lineage arising from a primary culture that can be maintained in culture for an unlimited time. The cells can contain introduced, e.g., via transformation, transfection, infection, or injection, expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in J. Sambrook et al., 2012, *Molecular Cloning, A Laboratory Manual*, 4$^{th}$ edition Cold Spring Harbor Press, Plainview, N.Y. or any of the previous editions; F. M. Ausubel et al., 2013, Current *Protocols in Molecular Biology*, John Wiley & Sons, New York, N.Y, or any of the previous editions; Kaufman, R. J., *Large Scale Mammalian Cell Culture*. 1990, all of which are incorporated herein for any purpose.

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or other factors, such as those described herein. The cells are typically selected that can express and secrete proteins, or that can be molecularly engineered to express and secrete, large quantities of a particular protein, more particularly, a glycoprotein of interest, into the culture medium. It will be understood that the protein produced by a host cell can be endogenous or homologous to the host cell. Alternatively, the protein is heterologous, i.e., foreign, to the host cell, for example, a human protein produced and secreted by a Chinese hamster ovary (CHO) host cell. Additionally, mammalian proteins, i.e., those originally obtained or derived from a mammalian organism, are attained by the methods the present invention and can be secreted by the cells into the culture medium.

The compositions of the present invention can be used to culture a variety of cells. In one embodiment, the cultured cells are eukaryotic cells such as plant and/or animal cells. The cells can be mammalian cells, fish cells, insect cells, amphibian cells or avian cells. A wide variety of mammalian cell lines suitable for growth in culture are available from the American Type Culture Collection (Manassas, Va.) and other depositories as well as commercial vendors. Cell that can be used in the processes of the invention include, but not limited to, MK2.7 cells, PER-C6 cells, Chinese hamster ovary cells (CHO), such as CHO-K1 (ATCC CCL-61), DG44 (Chasin et al., 1986, *Som. Cell Molec. Genet.*, 12:555-556; Kolkekar et al., 1997, *Biochemistry*, 36:10901-10909; and WO 01/92337 A2), dihydrofolate reductase negative CHO cells (CHO/–DHFR. Urlaub and Chasin, 1980, *Proc. Natl. Acad. Sci. USA,* 77:4216), and dp12.CHO cells (U.S. Pat. No. 5,721,121): monkey kidney cells (CV1, ATCC CCL-70); monkey kidney CV1 cells transformed by SV40 (COS cells, COS-7, ATCC CRL-1651); HEK 293 cells, and Sp2/0 cells, 5 L8 hybridoma cells, Daudi cells, EL4 cells, HeLa cells. HL-60 cells, K562 cells, Jurkat cells, THP-1 cells, Sp2/0 cells, primary epithelial cells (e.g., keratinocytes, cervical epithelial cells, bronchial epithelial cells, tracheal epithelial cells, kidney epithelial cells and retinal epithelial cells) and established cell lines and their strains (e.g., human embryonic kidney cells (e.g., 293 cells, or 293 cells subcloned for growth in suspension culture, Graham et al., 1977, *J. Gen. Virol.,* 36:59); baby hamster kidney cells (BHK, ATCC CCL-10); mouse sertoli cells (TM4, Mather, 1980, *Biol. Reprod.,* 23:243-251): human cervical carcinoma cells (HELA, ATCC CCL-2); canine kidney cells (MDCK, ATCC CCL-34): human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals NY Acad. Sci.,* 383:44-68); MCR 5 cells; FS4 cells; PER-C6 retinal cells, MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells. T24 cells, WI-28 VA13, 2RA cells, WISH cells. BS-C-I cells, LLC-MK$_2$ cells, Clone M-3 cells, 1-10 cells, RAG cells, TCMK-1 cells, Y-1 cells, LLC-PKI cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CV-1 cells, COS-1 cells, COS-3 cells, COS-7 cells, African green monkey kidney cells (VERO-76, ATCC CRL-1587; VERO, ATCC CCL-81); DBS-FrhL-2 cells, BALB/3T3 cells, F9 cells, SV-T2 cells, M-MSV-BALB/3T3 cells, K-BALB cells, BLO-11 cells, NOR-10 cells, $C_3H/IO/T2$ cells, $HSDM_1C_3$ cells, KLN205 cells, McCoy cells, Mouse L cells, Strain 2071 (Mouse L) cells, L-M strain (Mouse L) cells, L-MTK (Mouse L) cells, NCTC clones 2472 and 2555, SCC-PSA1 cells, Swiss/3T3 cells, Indian muntac cells, SIRC cells, $C_H$ cells, and Jensen cells, or derivatives thereof) or any other cell type known to one skilled in the art.

Cells may be suitable for adherent, monolayer and/or suspension culture, transfection, and expression of proteins, for example, antibodies. The cells can be used, for example, with batch, fed batch and perfusion or continuous culture methods.

Types of Cell Cultures

For the purposes of understanding, yet without limitation, it will be appreciated by the skilled practitioner that cell cultures and culturing runs for protein production can include batch culture, fed-batch culture, perfusion culture, or combinations thereof. In batch culture, cells are initially cultured in medium and this medium is not removed, replaced, or supplemented, i.e., the cells are not "fed" with fresh medium, during or before the end of the culturing run. The entire cell culture is harvested at the end of the culturing run.

For fed-batch cultures, the culturing run time is increased by supplementing the culture medium periodically or continuously with fresh medium during the run, i.e., the cells are "fed" with new medium ("fed medium") during the culturing run. Fed-batch cultures can include the various feeding regimens and times as described above, for example, daily, every other day, every two days, etc., more than once per day, or less than once per day, and so on. Further, fed-batch cultures can be fed continuously with feeding medium. The desired product is then harvested at the end of the culturing run.

Perfusion culture, sometimes known as continuous culture, is one in which the cell culture receives the addition of fresh medium ("perfusion medium") and spent medium is removed from the bioreactor. Perfusion can be continuous, step-wise, intermittent, or a combination of any or all of any of these. Perfusion rates can be less than a working volume to many working volumes per day. The term "perfusion flow rate" is the amount of media that is passed through (added and removed) from a bioreactor, typically expressed as some portion of or a multiple of the working volume, in a given time. "Working volume" refers to the amount of bioreactor volume used for cell culture. In one embodiment the perfusion flow rate is one working volume or less per day. Perfusion feed medium can be formulated to maximize perfusion nutrient concentration to minimize perfusion rate.

Preferably the cells are retained in the culture and the spent medium that is removed is substantially free of cells or has significantly fewer cells than the cell culture. Recombinant proteins expressed by the cell culture may be retained or removed from the cell culture, depending on the retention system used. Sometimes it is preferable for the host cells and the expressed recombinant proteins to remain in the retentate in the bioreactor and for the permeate be substantially free of or have significantly less of either ("null permeate"). Other times it may be preferable to retain cells but allow the expressed proteins to pass into the permeate ("harvest permeate").

Perfusion can be accomplished by a number of means including centrifugation, sedimentation, or filtration, See e.g. Voisard et al., (2003), Biotechnology and Bioengineering 82:751-65. In one embodiment a filtration method is used. Filters include membrane filters, ceramic filters and metal filters and may be in any shape, including spiral wound or tubular or in the form of a sheet. One or more filters can be connected to, in fluid communication with, a bioreactor together or independently, in series or in parallel.

Hollow fiber filters are used in mammalian cell perfusion culture for cell and/or recombinant protein product retention. When the cell culture, including cell culture media, cells (whole and lysed), soluble expressed recombinant proteins, host cell proteins, waste products and the like, are introduced to the filter, depending on the pore size or molecular weight cutoff (MWCO) the hollow fiber material may retain certain cell culture components on the lumen side (inside) and allow certain components to pass through the filter (permeate) based on the pore size or molecular weight cutoff of the hollow fiber material. The material that is retained (retentate) is returned to the bioreactor. Fresh perfusion cell culture media is added to the bioreactor and permeate is withdrawn from the filter at predetermined intervals or continuously to maintain a desired or constant bioreactor volume. The permeate can be discarded, stored in holding tanks, bags or totes or transferred directly to another unit operation, such as filtration, centrifugation and/or other downstream purification methods or the like. Hollow fibers for microfiltration typically have a pore size ranging from 0.1 μm to 5-10 μm or a molecular weight cut off of 500 kDa or more and can be used to allow the protein to pass through into the permeate. Ultrafiltration hollow fibers typically have a pore size range of 0.01 μm to 0.1 μm or a molecular weight cut off of 300 kDa or less, and can be used to retain the desired protein in the retentate and return it back to the bioreactor. This can be used, for example, to concentrate the recombinant protein product for harvest. Such filters are available commercially, such as Xampler UFP-750-E-4MA, Xampler UFP-30-E-4MA, (GE Healthcare, Pittsburgh, Pa.) and Midikros TC Modules T02-E030-10. T02-050-10, T02-E750-05, T02-M10U-06 (Spectrum Laboratories, Inc, Dominguez, Calif.).

The invention provides that when the null permeate is collected, the filter is a hollow fiber filter having a pore size or molecular weight cut off that does not allow the recombinant protein product to pass into the permeate and instead retains it in the bioreactor. The invention also provides that when the harvest permeate is collected, the filter is a hollow fiber filter having a pore size or molecular weight cut off that allows the recombinant protein to pass through the hollow fiber.

The cell culture is drawn out of the bioreactor and into the filter by a pumping system, which passes the cell culture through the lumen side of the hollow fiber. Examples of cell pumping systems include peristaltic pumps, double diaphragm pumps, low shear pumps (Levitronix® pumps, Zurich, Switzerland) and alternating tangential flow systems (ATF™, Refine Technology. Pine Brook, N.J., See e.g. U.S. Pat. No. 6,544,424; Furey (2002) Gen. Eng. News, 22 (7), 62-63). The permeate may be drawn from the filters by use of peristaltic pumps.

Single Unit Filter System

The invention provides a single unit filter system comprising two or more hollow fiber filter components of different pore sizes or molecular weight cutoffs combined in series in a single unit filter system, optionally contained within a housing, which can be operated by a single cell pumping device. This allows for collection in a product retention mode (removing null permeate) or a product collection mode (removing harvest permeate) via one filter system (FIG. 1). The single unit filter system offers the advantages of removing host cell proteins and other waste from the cell culture during harvest cycles, prolonging the duration of the cell culture. The single unit filter system has potentially less filter fouling for greater harvest efficiency. The single unit filter system can provide permeate in multiple, smaller batches for easier and efficient loading of downstream purification columns. The single unit filter system may be used as part of a continuous manufacturing process.

The configuration of the single unit filter system includes two or more hollow fiber filter components having different pore sizes or molecular weight cutoffs, configured in series, such that the all the filters are in fluid communication with each other and the bioreactor and may be operated by a single pumping device. Such hollow fiber filter components are commercially available from GE Healthcare and Spectrum Laboratories, Inc., for example. While the cell culture flows through all filters, permeate may be selectively removed from one or more filters at a time. The permeate (null or harvest) is removed by withdrawing permeate from the appropriate hollow fiber component based its pore size or molecular weight cutoff. Null permeate and harvest permeate are removed separately and independently by use of individual peristaltic pumps. Timing and ratio of permeate collection can be controlled through their separate peristaltic pumps.

The individual hollow fiber filter components may be aligned in any configuration that is suitable for the application. In one embodiment the hollow fiber filter component(s) having a pore size or molecular weight cutoff such that the recombinant protein product of the cell culture is retained in the retentate in the cell culture bioreactor is placed such that it is the first to receive the cell culture flow from the bioreactor.

The configuration of the single unit filter system allows the harvest permeate and null permeate to be removed from the bioreactor in a segregated manner and in a manner such that the relative volumetric ratio and timing of removal can be controlled as desired. The permeate is collected from the single unit filter system at the same rate as the perfusion rate.

In addition to using commercially available hollow fiber filter components the hollow fiber material may be constructed having two separate zones within a single filter which are isolated from each other with by a potting zone. Also, separate hollow fibers having different pore size or molecular weight cutoff may be joined by a connector zone in a middle potting area to isolate the two permeate sides. Each pore size domain, over the length of the hollow fiber, would have the corresponding shell sides isolated from the other pore size shell side domains so that permeate could be withdrawn from each pore size shell side domain independent of the others.

The filters may be secured to each other by any method that allows for fluid communication between the hollow fiber filter components. The filter components may be glued or welded together. The filters may be joined together by a clamp, such as a tri claim, or other mechanical device that secures the filter units together and allows for fluid communication between the filters. The filter housing may be provided with internal and external threaded regions to be used to join the filter units, either directly or through a threaded coupler. Filters may also be connected by any type of locking mechanism.

Positioning two filters directly end to end may create a tight junction or a slight misalignment between the hollow fibers that could impede cell flow and cause cell damage due to shear. As a result, there could be a drop in viability due to the alignment of the filters. A spacer or coupler which provides for some distance between the adjacent filter units, allowing for the flow of cells to transition more easily between the lumen of one filter into the lumen of the next hollow fiber may be used between filter units. The spacer separates the individual filter units from one another, allowing for a sterile flow path between the individual hollow fibers while also maintaining the isolation of the respective hollow shell sides from which the permeate with withdrawn.

Such spacers may be made from any material that would make a secure and sterile connection between the filters and allow for fluid communication between the filters. Such spacers may be self-sealing to the filters. The spacers may be glued or welded to the filters being joined. The spacer may secured to the filters by a mechanical device that secures the spacer to the filters, such as a clamp. The spacer may be provided with internal or external threaded regions to be used to secure the spacer to the filters directly or through a threaded coupler. The spacer may also be connected by any type of locking mechanism.

The single unit filter system may be optionally enclosed by an outer housing for ease of use, especially when more than two filters are configured in series. The outer housing may be made of plastic or other suitable material that will maintain a sterile barrier to the material inside the filter unit. The housing may be a secondary enclosure made to fit over commercially available hollow fiber filters or the housing may be manufactured as the primary housing for the connected hollow fiber filters. The housing should have sufficient openings to allow for introduction and collection of feed and retentate as well at least one permeate port for each hollow fiber filter having a different pore size or molecular weight cut off.

The single unit filter system may be used in conjunction with a single cell pumping system which passes the cell culture through the lumen side of the hollow fiber at a constant flow rate, has described above.

Cell Culture Processes

Cell culture can be carried out under conditions that accommodate small to large scale production of recombinant proteins using culture vessels and/or culture apparatuses that are conventionally employed for animal or mammalian cell culture. For culturing on a larger scale, equipment such as roller bottle systems, packed bed type culture devices, fermentor type tank bioreactors, air lift type bioreactors, fluidized bed bioreactors, immobilized cell bioreactors, hollow fiber bioreactors, stirred tank bioreactors, multistage bioreactors, centrifugal bioreactors or any other suitable devise known to one skilled in the art can be used. Single use bioprocessing equipment, such as single use bioreactors may also be used. Microcarriers may also be used with bioreactor systems. The systems can be operated in a batch, fed-batch or perfusion/continuous mode. In addition, the culture vessels may be equipped with additional apparatus such a cell separators using filters, gravity, centrifugal force, and the like.

The term "growth phase" of a cell culture refers to the period of exponential cell growth (i.e., the log phase) where the cells are generally rapidly dividing. Cells are maintained at the growth phase for a period of about one day, or about two days, or about three days, or about four days, or longer than four days. The duration of time for which the cells are maintained at growth phase will vary based on the cell-type, the rate of growth of cells and/or the culture conditions, for example.

The term "transition phase" refers to the period between the growth phase and the production phase. Generally, transition phase is the time during which culture conditions may be controlled to support a shift from growth phase to production phase. Various cell culture parameters may be monitored or manipulated to control the shift, including but are not limited to one or more of, temperature, osmolality, concentrations of vitamins, amino acids, sugars, ammonium, lactic acid, and salts or the like.

The term "production phase" refers to the period of time where the cell growth is/has plateaued. The logarithmic cell growth typically decreases before or during this phase and protein production takes over. Fed batch and perfusion cell culture processes supplement the cell culture medium or provide fresh medium during this phase to achieve and/or maintain desired cell density, viability and/or recombinant protein product titer. A production phase can be conducted at large scale. Large scale cell cultures can be maintained in a volume of at least about 100, 500, 1000, 2000, 3000, 5000, 7000, 8000, 10.000, 15.000, 20,000 liters or more. In a preferred embodiment the production phase is conducted in 500 L, 1000 L and/or 2000 L bioreactors.

The production of recombinant proteins can be done in multiple phases. In a multiple phase process, cells are cultured in two or more distinct phases. Typically cells are first cultured in one or more growth phases, under environmental conditions that maximize cell proliferation and viability, then transitioned to a production phase, under environmental conditions that maximize protein production. In a commercial process for production of recombinant proteins by mammalian cells, there are commonly multiple, for example, at least about 2, 3, 4, 5, 6, 7, 8, 9, 10 or more growth phases that occur in different culture vessels (N-x to N-1) preceding the final production culture. The growth and production phases may be preceded by, or separated by, one or more transition phases. A production phase can be conducted at large scale. The method according to the present invention may be used to extend the production phase of a cell culture.

When preparing for commercial production of a recombinant protein, the cell cultures that precede a final production culture typically go through two processes, a seed train and an inoculum train. The seed train phase (N-X) takes place at small scale where cells are quickly expanded in number. At the inoculum train phase (N-1), cells are further expanded to generate the inoculum for the production bioreactor. Seed and N-1 trains can be produced by any culture method, typically batch cell cultures. N-1 cell densities of $>15 \times 10^6$ cells/mL are typical for seeding production bioreactors. Higher N-1 cell densities and/or adjusting the cell culture media can decrease or even eliminate the time needed to reach a desired cell density in the production bioreactor. In one embodiment higher N-1 cell densities are achieved via perfusion culture using alternating tangential flow filtration. An N-1 cell culture grown by means of a perfusion process using alternating tangential flow filtration can provide cells at any desired density, high cell densities such as densities of $>90 \times 10^6$ cells/mL or more, can be easily achieved. The N-1 cell culture can be used to generate a single bolus inoculation culture or can be used as a rolling seed stock culture that is maintained to inoculate multiple production bioreactors. The inoculation density can have a positive impact on the level of recombinant protein produced. Recombinant protein product levels tend to increase with increasing inoculation density. Improvement in titer is tied not only to higher inoculation density, but is likely to be influenced by the metabolic and cell cycle state of the cells that are placed into production. During the N-1 process the cell culture may be allowed to enter a production phase prior to inoculation into the production bioreactor. Such inoculation allows for production to begin immediately in the production bioreactor.

The term "cell density" refers to the number of cells in a given volume of culture medium. "Viable cell density" refers to the number of live cells in a given volume of culture medium, as determined by standard viability assays (such as trypan blue dye exclusion method). The term "packed cell volume" (PCV), also referred to as "percent packed cell volume" (% PCV), is the ratio of the volume occupied by the cells, to the total volume of cell culture, expressed as a percentage (see Stettler, et al., (2006) Biotechnol Bioeng. December 20:95(6):1228-33). Packed cell volume is a function of cell density and cell diameter, increases in packed cell volume could arise from increases in cell density or cell diameter or both. Packed cell volume is a measure of the solid content in the cell culture. Since host cells vary in size and cell cultures also contain dead and dying cells and other cellular debris, packed cell volume can describe with a greater degree of accuracy the solid content within a cell culture. For example, a 2000 L culture having a cell density of $50 \times 10^6$ cells/ml would have vastly different packed cell volumes depending on the size of the cells. In addition, some cells will increase in size, such as when in a growth arrested state, so the packed cell volume prior to growth-arrest and post growth-arrest will likely be different, due to increase in biomass as a result to cell size increase. Lower packed cell volume during the production phase helps mitigate dissolved oxygen sparging problems that can hinder higher cell density perfusion cultures. The lower packed cell volume also allows for a smaller media volume which allows for the use of smaller media storage vessels and can be combined with slower flow rates. Lower packed cell volume also has less impact on harvest and downstream processing, compared to higher cell biomass cultures. All of which reduces the costs associated with manufacturing recombinant protein therapeutics.

In one embodiment the method further comprises that the packed cell volume during a production phase is less than or equal to 35%. In a related embodiment the packed cell volume is less than or equal to 30%.

In one embodiment the viable cell density of the mammalian cell culture at a packed cell volume less than or equal to 35% is $10 \times 10^6$ viable cells/ml to $80 \times 10^6$ viable cells/ml. In a related embodiment the viable cell density of the mammalian cell culture is $20 \times 10^6$ viable cells/ml to $30 \times 10^6$ viable cells/ml.

Cell Culture Controls

Cell culture conditions suitable for the methods of the present invention are those that are typically employed and known for batch, fed-batch, or perfusion (continuous) culturing of cells or any combination of those methods, with attention paid to pH, dissolved oxygen ($O_2$), and carbon dioxide ($CO_2$), agitation and humidity, and temperature. During recombinant protein production it is desirable to have a controlled system where cells are grown for a desired time or to a desired density and then the physiological state of the cells is switched to a growth-limited or arrested, high productivity state where the cells use energy and substrates to produce the recombinant protein in favor of increasing cell density. For commercial scale cell culture and the manufacture of biological therapeutics, the ability to limit or arrest cell growth and being able to maintain the cells in a growth-limited or arrested state during the production phase is very desirable. Such methods include, for example, temperature shifts, use of chemical inducers of protein production, nutrient limitation or starvation and cell cycle inhibitors, either alone or in combination.

Once such mechanism for limiting or arresting growth is to shift the temperature during the cell culture. For example, a growth phase may occur at a higher temperature, shifting to a lower temperature may initiate and/or maintain a production phase. For example, a growth phase may occur at a first temperature set-point from about 35° C. to about 38° C., and a production phase may occur at a second temperature set-point from about 29° C. to about 37° C., optionally from about 30° C. to about 36° C. or from about 30° C. to about 34° C.

Switching the temperature set-point can be done manually or can be done automatically by making use of bioreactor control systems. The temperature set-point may be switched at a predetermined time or in response to one or more cell culture parameters, such as cell density, titer, or concentration of one or more media components. One such method uses an online biomass monitoring tool integrated into the bioreactor control system to trigger a temperature set-point change when a desired cell density is reached. For example, a capacitance based biomass probe may be used for online cell density estimation and the data from online measurements can be used to trigger a shift in the bioreactor temperature. Such capacitance based probes include Fogale capacitance sensor (DN12-200) (Nimes. France).

In addition, chemical inducers of protein production, such as caffeine, butyrate, and/or hexamethylene bisacetamide (HMBA), may be added at the same time as, before, or after a temperature shift. If inducers are added after a temperature shift, they can be added from one hour to five days after the temperature shift, optionally from one to two days after the temperature shift. The cell cultures can be maintained for days or even weeks while the cells produce the desired protein(s).

Another method to maintain cells at a desired physiological state is to induce cell growth-arrest by exposure of the cell culture to low L-asparagine conditions and/or asparagine starvation (see e.g., WIPO Publication No. WO 2013/006479). Cell growth-arrest may be achieved and maintained through a culture medium that contains a limiting concentration of L-asparagine and maintaining a low concentration of L-asparagine in the cell culture. Maintaining the concentration of L-asparagine at 5 mM or less can be used to induce and maintain cells in a growth-arrested state whereby productivity is increased.

Cell cycle inhibitors, compound known or suspected to regulate cell cycle progression and the associated processes of transcription, DNA repair, differentiation, senescence and apoptosis related to this are also useful to induce cell growth-arrest. Cell cycle inhibitors that interact with the cycle machinery, such as cyclin-dependent kinases (CDKs) are useful as are those molecules that interact with proteins from other pathways, such as AKT, mTOR, and other pathways that affect, directly or indirectly, the cell cycle.

Harvest and Purification

The expressed recombinant proteins may be secreted into the culture medium from which they can be recovered and/or collected. The recombinant proteins may then be subjected on one or more processing steps including harvest, purification, endotoxin and/or viral inactivation/filtration, ultrafiltration/diafiltration into a suitable pharmaceutical formulation and/or storage The expressed recombinant proteins may be captured in the harvest permeate. The proteins may be purified, or partially purified, from harvest permeates using processes and commercially available products known in the art and/or available from commercial vendors. Such methods include flocculation; centrifugation; precipitation; filtration methods such as depth filtration; chromatography methods including, affinity chromatography, size exclusion chromatography, ion exchange chromatography, mixed mode anion exchange chromatography, hydrophobic interaction chromatography and hydroxyapatite chromatography, among other available methods.

The purified proteins can then be "formulated", meaning buffer exchanged, sterilized, bulk-packaged, and/or packaged for a final user. Suitable formulations for pharmaceutical compositions include those described in *Remington's Pharmaceutical Sciences*, 18th ed. 1995, Mack Publishing Company, Easton, Pa.

Process Analytical Techniques

Process analytical technologies and methods are available to monitor and evaluate samples taken during cell culture and purification processes to quantitatively and/or qualitatively monitor characteristics of the recombinant protein and the production process. This real time or inline information can be used to monitor and/or control product and production parameters, such as titer, cell density; product quality attributes such as post translational modifications: product or process variability such as impurities and the like, to make timely decisions and modify processes as necessary. For example product quality attributes such as distribution of glycan species, oxidation levels or deamidation can be monitored and/or controlled.

Each step of an upstream cell culture process or a downstream purification process may be monitored to provide information about the amount of a particular product quality attribute (PQA) and to control this PQA with a preset target and range.

Samples may be taken intermittently, at desired frequencies, or continuously. Samples may be analyzed in real time or near real time or stored for later analysis. This information can be used to make changes during upstream and downstream processes.

Detection of product quality attribute may be done using mass spectrometry, liquid chromatography with UV and/or mass spectrometry detection and capillary electrophoresis and the like.

These processes are adaptable to continuous monitoring with manual or automated process adjustments such as feeds, temperature, process duration as determined by the level of a specified product quality attribute.

Intact mass analysis to detect the presence of post-translational modifications such as amino acid processing and glycosylation may be made using a polyhydroxyethyl aspartamide column operated in size-exclusion mode and coupled with ESI-MS (Brady et al., (2008) J Am Soc Mass Spectro, 19: 502-509).

Real-time monitoring eluate from ion exchange chromatography by monitoring a normalized LS/UV ratio for each fraction using laser light scattering detector and an UV absorbance, see US Patent Publication No. US 2013-0303732.

Multi attribute method makes use of single liquid-chromatography/mass spectrometry (LC/MS) to search and characterize tandem MS data using various database and search platforms such as Sequest (The Scripps Research Institute, La Jolla, Calif.), X!Tandem (The Global Proteome Machine Organization) or Mascot (Matrix Science, Boston, Mass.). Samples may be denatured at high pH or to maintain disulfide isoforms and protect succinimide variants, at low pH. The sample is then reduced and alkylated followed by digestion with trypsin. The sample is then injected into an MS (such as a Q Exactive™ Hybrid Quadrupole-Orbitrap Mass Spectrometer, Thermo Fischer Scientific, Waltham, Mass.) and analysis is performed using Pinpoint software (Thermo Fischer Scientific). Attributes that can be identified, quantified and monitored include isomerization, deamination, disulfide reduction, host cell protein contamination, mutations, misincorporations, hydroxylysine, thioether, non-glycolysated heavy chains, C-terminal amidation, residual protein A, characterize glycans and provide molecule identity. The mass accuracy for each attribute monitored can be set at less than 5 ppm of the predicted mass. Identification of the peptide/attribute is confirmed by MS2 fragmentation and orthogonal characterization methods (HILIC-MS for glycosylation for example). The experimental isotopic distribution must have a dot product score better than 0.95 when compared to the theoretical isotopic distribution. A retention time window is set for each attribute and all detectable charge states for each attribute are considered for quantification. A criteria is defined that will detect changes in the attribute. For example, deamination can be monitored by determining a deamination value (deaminated peptide divided by the sum of the deaminated peptide and the unmodified parent peptide multiplied by 100. Glycosylation can be monitored by comparing each specific glycan to the sum of all detectable glycans.

In some embodiments process analytical technologies may also include "product attribute control" (PAC). PAC combines multiple PAT elements with a model of the bioprocess to enact real time feedback control of one or more CQAs. This new PAC process is an example of implementation of QbD production of biopharmaceuticals. The PAC process draws on the use of a control lever that can impact the CQA. The control lever is incorporated into a model based control loop to maintain the CQA at the desired target as specified in the QTPP. Specifically, a control lever is an adjustment to a process parameter that impacts a CQA in a way that can be modeled mathematically. For example, levels of an inhibitor or activator could be dynamically adjusted to regulate a glycosylation enzyme activity to regulate the glycosylation profile of a product, provided their impact can be modeled mathematically. Likewise temperature or pH could be adjusted during a run provided their impact on CQAs can also be reliably modeled.

Proteins

As used herein "peptide," "polypeptide" and "protein" are used interchangeably throughout and refer to a molecule comprising two or more amino acid residues joined to each other by peptide bonds. Peptides, polypeptides and proteins are also inclusive of modifications including, but not limited to, glycosylation, lipid attachment, sulfation, gamma-carboxylation of glutamic acid residues, hydroxylation and ADP-ribosylation.

Proteins can be of scientific or commercial interest, including protein-based drugs. Proteins include, among other things, antibodies, fusion proteins, and cytokines. Peptides, polypeptides and proteins may be produced by prokaryote and eukaryote cell lines using cell culture methods and may be referred to as "recombinant peptide", "recombinant polypeptide", "recombinant protein", "recombinant protein product" and "product". The expressed protein(s) may be produced intracellularly or secreted into the culture medium from which it can be recovered and/or collected.

Nonlimiting examples of mammalian proteins that can be advantageously produced by the methods of this invention include proteins comprising amino acid sequences identical to or substantially similar to all or part of one of the following proteins: tumor necrosis factor (TNF), flt3 ligand (WO 94/28391), erythropoeitin, thrombopoeitin, calcitonin, IL-2, angiopoietin-2 (Maisonpierre et al. (1997), *Science* 277(5322): 55-60), ligand for receptor activator of NF-kappa B (RANKL, WO 01/36637), tumor necrosis factor (TNF)-related apoptosis-inducing ligand (TRAIL, WO 97/01633), thymic stroma-derived lymphopoietin, granulocyte colony stimulating factor, granulocyte-macrophage colony stimulating factor (GM-CSF, Australian Patent No. 588819), mast cell growth factor, stem cell growth factor (U.S. Pat. No. 6,204,363), epidermal growth factor, keratinocyte growth factor, megakaryote growth and development factor, RANTES, human fibrinogen-like 2 protein (FGL2; NCBI accession no. NM_00682: Rüegg and Pytela (1995), *Gene* 160:257-62) growth hormone, insulin, insulinotropin, insulin-like growth factors, parathyroid hormone, interferons including α-interferons, γ-interferon, and consensus interferons (U.S. Pat. Nos. 4,695,623 and 4,897,471), nerve growth factor, brain-derived neurotrophic factor, synaptotagmin-like proteins (SLP 1-5), neurotrophin-3, glucagon, interleukins, colony stimulating factors, lymphotoxin-D, leukemia inhibitory factor, and oncostatin-M. Descriptions of proteins that can be produced according to the inventive methods may be found in, for example, *Human Cytokines: Handbook for Basic and Clinical Research*, Volumes 1-3 (Aggarwal and Gutterman, eds. Blackwell Sciences, Cambridge, Mass., 1998); *Growth Factors: A Practical Approach* (McKay and Brown, eds., Oxford University Press Inc., New York, 1998) all editions; and *The Cytokine Handbook*. Vols. 1 and 2 (Thompson and Lotze eds., Academic Press, San Diego, Calif., 2003).

Additionally the methods of the invention would be useful to produce proteins comprising all or part of the amino acid sequence of a receptor for any of the above-mentioned proteins, an antagonist to such a receptor or any of the above-mentioned proteins, and/or proteins substantially similar to such receptors or antagonists. These receptors and antagonists include: both forms of tumor necrosis factor receptor (TNFR, referred to as p55 and p75, U.S. Pat. Nos. 5,395,760 and 5,610,279), Interleukin-1 (IL-1) receptors (types I and II; EP Patent No. 0460846, U.S. Pat. Nos. 4,968,607, and 5,767,064), IL-1 receptor antagonists (U.S. Pat. No. 6,337,072), IL-1 antagonists or inhibitors (U.S. Pat. Nos. 5,981,713, 6,096,728, and 5,075,222) IL-2 receptors, IL-4 receptors (EP Patent No. 0 367 566 and U.S. Pat. No. 5,856,296), IL-15 receptors, IL-17 receptors, IL-18 receptors, Fc receptors, granulocyte-macrophage colony stimulating factor receptor, granulocyte colony stimulating factor receptor, receptors for oncostatin-M and leukemia inhibitory factor, receptor activator of NF-kappa B (RANK, WO 01/36637 and U.S. Pat. No. 6,271,349), osteoprotegerin (U.S. Pat. No. 6,015,938), receptors for TRAIL (including TRAIL receptors 1, 2, 3, and 4), and receptors that comprise death domains, such as Fas or Apoptosis-Inducing Receptor (AIR).

Other proteins that can be produced using the invention include proteins comprising all or part of the amino acid sequences of differentiation antigens (referred to as CD proteins) or their ligands or proteins substantially similar to either of these. Such antigens are disclosed in *Leukocyte Typing VI* (*Proceedings of the VIth International Workshop and Conference*, Kishimoto, Kikutani et al., eds., Kobe, Japan, 1996). Similar CD proteins are disclosed in subsequent workshops. Examples of such antigens include CD22, CD27, CD30, CD39, CD40, and ligands thereto (CD27 ligand, CD30 ligand, etc.). Several of the CD antigens are members of the TNF receptor family, which also includes 41BB and OX40. The ligands are often members of the TNF family, as are 41BB ligand and OX40 ligand.

Enzymatically active proteins or their ligands can also be produced using the invention. Examples include proteins comprising all or part of one of the following proteins or their ligands or a protein substantially similar to one of these: a disintegrin and metalloproteinase domain family members including TNF-alpha Converting Enzyme, various kinases, glucocerebrosidase, superoxide dismutase, tissue plasminogen activator, Factor VIII, Factor IX, apolipoprotein E, apolipoprotein A-I, globins, an IL-2 antagonist, alpha-1 antitrypsin, ligands for any of the above-mentioned enzymes, and numerous other enzymes and their ligands.

The term "antibody" includes reference to both glycosylated and non-glycosylated immunoglobulins of any isotype or subclass or to an antigen-binding region thereof that competes with the intact antibody for specific binding, unless otherwise specified, including human, humanized, chimeric, multi-specific, monoclonal, polyclonal, and oligomers or antigen binding fragments thereof. Also included are proteins having an antigen binding fragment or region such as Fab, Fab', F(ab')$_2$, Fv, diabodies, Fd, dAb, maxibodies, single chain antibody molecules, complementarity determining region (CDR) fragments, scFv, diabodies, triabodies, tetrabodies and polypeptides that contain at least a portion of an immunoglobulin that is sufficient to confer specific antigen binding to a target polypeptide. The term "antibody" is inclusive of, but not limited to, those that are prepared, expressed, created or isolated by recombinant means, such as antibodies isolated from a host cell transfected to express the antibody.

Examples of antibodies include, but are not limited to, those that recognize any one or a combination of proteins including, but not limited to, the above-mentioned proteins and/or the following antigens: CD2, CD3, CD4, CD8, CD11a, CD14, CD18, CD20, CD22, CD23, CD25, CD33, CD40, CD44, CD52, CD80 (B7.1), CD86 (B7.2), CD147, IL-1α, IL-1β, IL-2, IL-3, IL-7, IL-4, IL-5, IL-8, IL-10, IL-2 receptor, IL-4 receptor, IL-6 receptor, IL-13 receptor, IL-18 receptor subunits, FGL2, PDGF-β and analogs thereof (see U.S. Pat. Nos. 5,272,064 and 5,149,792). VEGF, TGF, TGF-02, TGF-01, EGF receptor (see U.S. Pat. No. 6,235,883) VEGF receptor, hepatocyte growth factor, osteoprotegerin ligand, interferon gamma, B lymphocyte stimulator (BlyS, also known as BAFF, THANK, TALL-1, and zTNF4; see Do and Chen-Kiang (2002). *Cytokine Growth Factor Rev.* 13(1): 19-25), C5 complement, IgE, tumor antigen CA125, tumor antigen MUC1, PEM antigen, LCG (which is a gene product that is expressed in association with lung cancer), HER-2, HER-3, a tumor-associated glycoprotein TAG-72, the SK-1 antigen, tumor-associated epitopes that are present in elevated levels in the sera of patients with colon and/or pancreatic cancer, cancer-associated epitopes or proteins expressed on breast, colon, squamous cell, prostate, pancreatic, lung, and/or kidney cancer cells and/or on melanoma, glioma, or neuroblastoma cells, the necrotic core of a tumor, integrin alpha 4 beta 7, the integrin VLA-4, B2 integrins, TRAIL receptors 1, 2, 3, and 4, RANK, RANK ligand, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, parathyroid hormone, rNAPc2 (which is an inhibitor of factor VIIa-tissue factor), MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, sclerostin, L-selectin, Respiratory Syncitial Virus, human immunodeficiency virus (HIV), hepatitis B virus (HBV), *Streptococcus mutans*, and *Staphlycoccus aureus*. Specific examples of known antibodies which can be produced using the methods of the invention include but are not limited to adalimumab, bevacizumab, infliximab, abciximab, alemtuzumab, bapineuzumab, basiliximab, belimumab, briakinumab, canakinumab, certolizumab pegol, cetuximab, conatumumab, denosumab, eculizumab, gemtuzumab ozogamicin, golimumab, ibritumomab tiuxetan, labetuzumab, mapatumumab, matuzumab, mepolizumab, motavizumab, muromonab-CD3, natalizumab, nimotuzumab, ofatumumab, omalizumab, oregovomab, palivizumab, panitumumab, pemtumomab, pertuzumab, ranibizumab, rituximab, rovelizumab, tocilizumab, tositumomab, trastuzumab, ustekinumab, vedolizomab, zalutumumab, and zanolimumab.

The invention can also be used to produce recombinant fusion proteins comprising, for example, any of the above-mentioned proteins. For example, recombinant fusion proteins comprising one of the above-mentioned proteins plus a multimerization domain, such as a leucine zipper, a coiled coil, an Fc portion of an immunoglobulin, or a substantially similar protein, can be produced using the methods of the invention. See e.g. WO94/10308; Lovejoy et al. (1993), *Science* 259:1288-1293; Harbury et al. (1993), *Science* 262:1401-05: Harbury et al. (1994), *Nature* 371:80-83; Håkansson et al. (1999), *Structure* 7:255-64. Specifically included among such recombinant fusion proteins are proteins in which a portion of a receptor is fused to an Fc portion of an antibody such as etanercept (a p75 TNFR:Fc), and belatacept (CTLA4:Fc). Chimeric proteins and polypeptides, as well as fragments or portions, or mutants, variants, or analogs of any of the aforementioned proteins and polypeptides are also included among the suitable proteins, polypeptides and peptides that can be produced by the methods of the present invention.

While the terminology used in this application is standard within the art, definitions of certain terms are provided herein to assure clarity and definiteness to the meaning of the claims. Units, prefixes, and symbols may be denoted in their SI accepted form. Numeric ranges recited herein are inclusive of the numbers defining the range and include and are supportive of each integer within the defined range. The methods and techniques described herein are generally performed according to conventional methods well known in the art and as described in various general and more specific references that are cited and discussed throughout the present specification unless otherwise indicated. See, e.g., Sambrook et al. Molecular Cloning: A LaboratoryManual, 4$^{th}$ ed., Cold Spring Harbor Laboratory Press, Cold Spring Harbor, N.Y. (2012): Ausubel et al., *Current Protocols in Molecular Biology*, Greene Publishing Associates (1995), and Greenfield, *Antibodies: A Laboratory Manual*2$^{nd}$ ed., Cold Spring Harbor Laboratory Press, Cold Spring Harbor. N.Y. (2013), or any earlier editions. All documents, or portions of documents, cited in this application, including but not limited to patents, patent applications, articles, books, and treatises, are hereby expressly incorporated by reference. What is described in an embodiment of the invention can be combined with other embodiments of the invention.

The present invention is not to be limited in scope by the specific embodiments described herein that are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

Example 1

Extended Periodic Cell Culture Process

This experiment describes a cell culture process with extended periodic harvesting (X-PH) compared to an ultra-filteration culture process (UF). For the extended periodic process, perfusion was carried out using a single filter unit system comprising an ultrafilter having a pore size or MWCO such that the recombinant protein product of the cell culture was retained in the retentate in the cell culture bioreactor connected to a microfilter having a pore size or molecular weight cutoff such that the recombinant protein of interest was carried in the permeate and collected as product harvest. The perfusion was performed by drawing a recombinant protein-free permeate, or null permeate, from the ultrafilter component until a predetermined parameter was reached, in this case days in culture, at which time the perfusion was carried out by drawing a recombinant protein containing permeate, or harvest permeate, from the microfilter component, for a predetermined time. After the predetermined time had elapsed, the process was repeated. This cycle of retaining and harvesting the protein product was repeated until the culture was terminated.

For the ultrafiltration culture process, cells were cultured in a perfusion system using an ultrafilter with a pore size or molecular weight cutoff such that the recombinant protein product was retained in the retentate in the cell culture bioreactor and a recombinant protein-free permeate was collected. The retained recombinant protein product was recovered as a harvest from the bioreactor when the culture was terminated.

Extended Periodic Harvesting Culture Process (X-PH)

On day 0, CHO cells expressing a recombinant antibody were inoculated into two 2 L bioreactors (Applikon, Foster City, Calif.) at $1 \times 10^6$ viable cells/mL in a working volume of 1500 ml of a serum-free chemically-defined batch medium. The cultures were maintained at 36° C., DO at 48.0 mmHg, agitation at 350 RPM.

The cell cultures were initiated in batch mode, perfusion was started on day 2 using an ATF-2™ alternating tangential flow filtration system (Refine Technologies, Hanover, N.J.) using a 30 cm 30 kDa hollow fiber filter (XAMPLER™ UFP-30-E-4MA, GE Healthcare, Pittsburgh, Pa.) connected in series with a 30 cm 750 kDa hollow fiber filter (XAMPLER™ UFP-750-E-4MA, GE Healthcare). The filters were joined together with an approximately 1 inch long sanitary connector spool piece using sanitary clamps. The medium was a serum-free chemically-defined perfusion medium containing 1.5 g/L polyoxyethylene-polyoxypropylene block copolymer (KOLLIPHOR® P188 SAFC Biosciences, ST. Louis, Mo.).

The perfusion rate was increased gradually from 0.5 to 1.0 bioreactor working volume/day over the cell culture run and was uniform through the filter unit. Null and harvest permeates were collected, via independent perfusion pumps, at the same rate as the perfusion rate. Daily samples were taken from the bioreactor to assess the culture. Viable cell density (VCD) and viability were determined using Vi-Cell (Beckman Coulter, Brea, Calif.). Titer was measured by HPLC analysis.

For glycan analysis, protein-containing samples were collected and purified by Protein A. The purified samples were treated with PNGase-F and incubated at 37° C. for 2 hours to release the N-linked glycans. The enzymatically released glycans were labeled with 2-aminobenzoic acid (2-AA) at 80° C. for 75 minutes. Excess 2-AA label was then removed with a Glycoclean S cartridge. The samples were evaporated overnight and the resulting dry pellet was reconstituted with water for subsequent HILIC (hydrophilic interaction liquid chromatography) analysis. The glycans were injected and bound to the column in high organic conditions and eluted with an increasing gradient of an aqueous ammonium formate buffer. Fluorescence detection was used to monitor the glycan elution and the relative percentage of the major and minor glycan species were calculated.

Prior to day 11, null permeate, or non-product containing permeate, was continuously collected by drawing permeate from the 750 kDa ultrafilter using a peristaltic pump (Watson Marlow 120U/DV Falmouth, Cornwall, UK) and was discarded. Because of the filter size, the protein product of the cell culture was retained in the retentate in the cell culture bioreactor.

Harvest permeate, or product containing permeate, was collected at five separate predetermined times during the cell culture run, according to the schedule provided in Table 1. The harvest permeate was collected by drawing permeate from the 30 kDa microfilter using a peristaltic pump (Watson Marlow 120U/DV Falmouth, Cornwall, UK). The protein product of the cell culture was carried in the permeate and collected as part of the harvest permeate. The harvest permeate was evaluated for titer and product quality as described above. The harvest permeate was stored in permeate bags (RCBB-300, RIM Bio Inc., Seattle, Wash.).

TABLE 1

Harvest permeate collection schedule

| Harvest | Day | Collection Time (hours) |
| --- | --- | --- |
| 1 | 11 to 12 | 22 |
| 2 | 14 to 15 | 23 |
| 3 | 17 to 18 | 25 |
| 4 | 20 to 21 | 26 |
| 5 | 23 to 24 | 25 |

Immediately following the completion of the collection of the each of the harvest permeates, null permeate was again continuously collected from the 750 kDa ultrafilter filter and discarded. The culture was terminated following collection of the harvest permeate on day 24.

Ultrafilter Culture Process (UF)

On day 0, CHO cells expressing the same recombinant antibody as above were inoculated into four 2 L bioreactors (Applikon, Foster City, Calif.)) at $1 \times 10^6$ viable cells/mL in a working volume of 1500 ml of a serum-free defined batch medium.

The cell cultures were initiated in batch mode, perfusion was started on day 2 using an ATF-2™ alternating tangential flow filtration system (Refine Technologies, Hanover, N.J.) equipped a 60 kDa hollow fiber filter (XAMPLER™ UFP-30-E-4MA, GE Healthcare, Pittsburgh, Pa.). The medium was a serum-free defined perfusion medium containing 1 g/L pluronic polyoxyethylene-polyoxypropylene block copolymer (KOLLIPHOR® P188) SAFC Biosciences, ST. Louis, Mo.).

The perfusion rate increased gradually from 0.5 to 1.0 working volume/day over the cell culture run. Samples were taken daily to assess the culture. Viable cell density (VCD) and viability were determined using Vi-Cell (Beckman Coulter. Brea, Calif.). Titer was measured by HPLC analysis.

Permeate was collected at the same rate as the perfusion rate. Because of the filter size, the protein product of the cell culture was retained in the retentate in the cell culture bioreactor until harvested when the culture was terminated on day 15.

Figure 2:
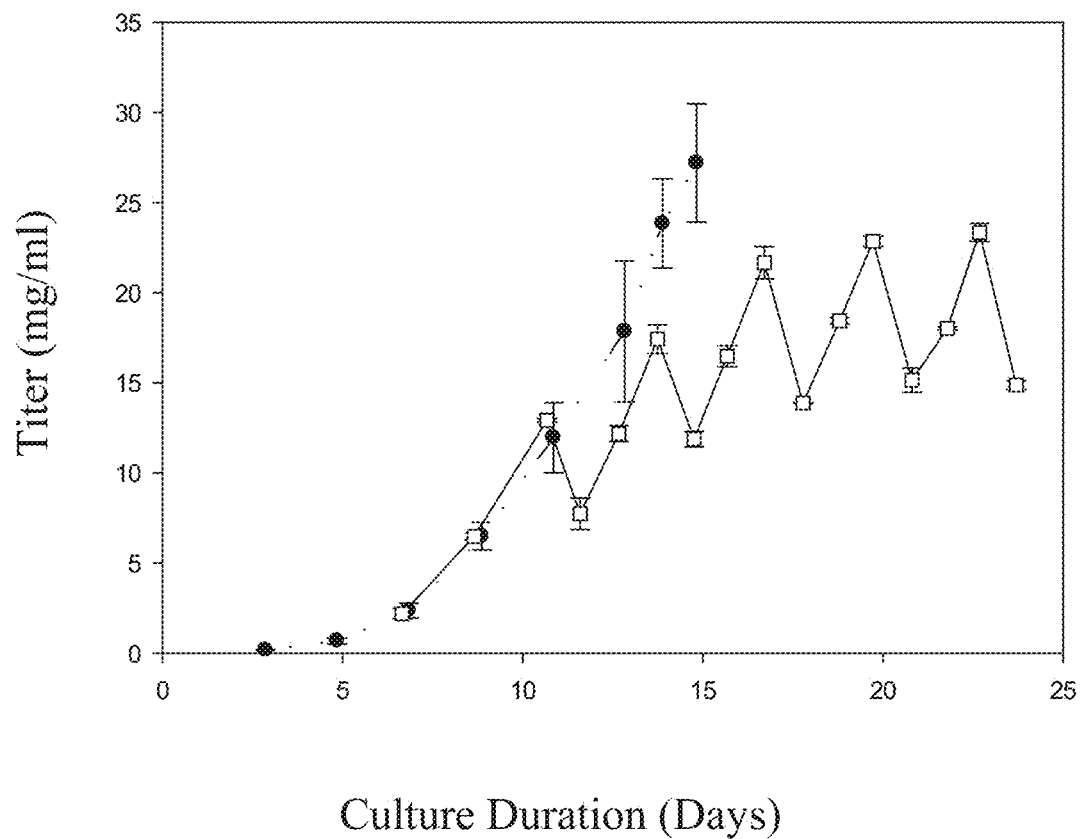
FIG. 2 Titer from extended periodic harvest process, n=2 (open square) compared to ultrafilteration process, n=4 (closed circle).
Figure 3:
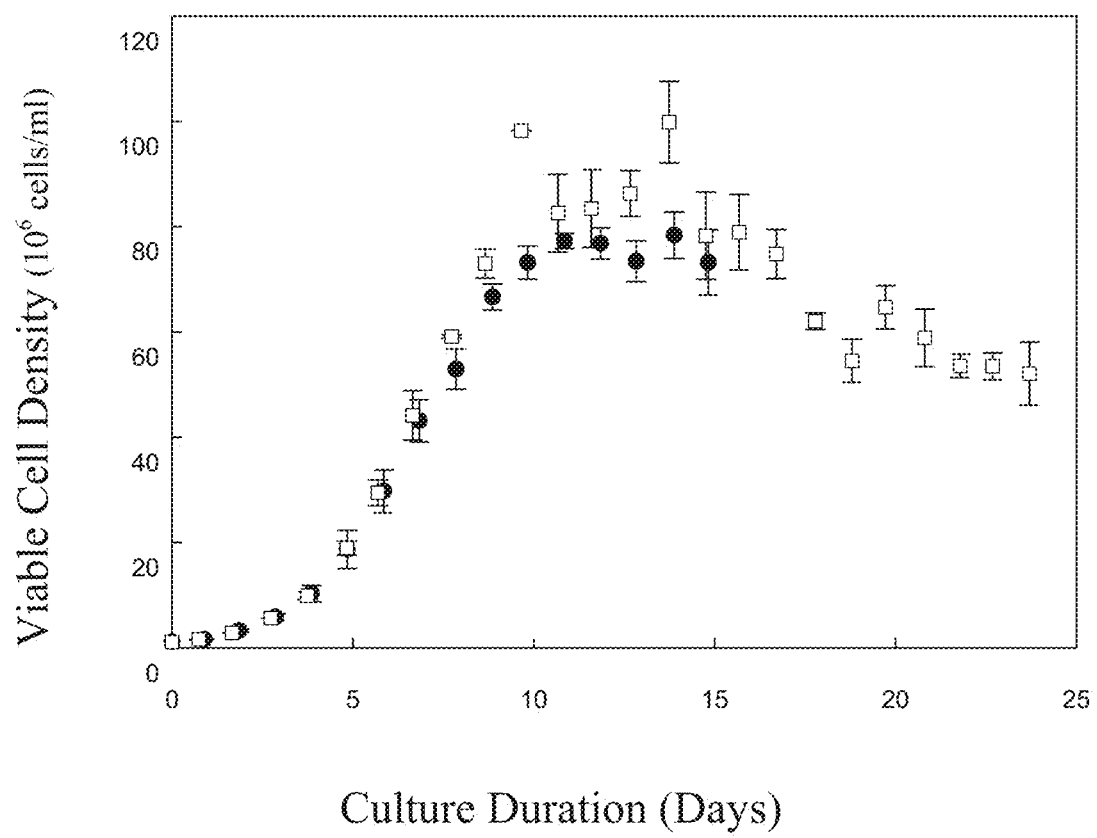
FIG. 3 Viable cell density from extended periodic harvest process, n=2 (open square) compared to ultrafiltration process, n=4 (closed circle).
Figure 4:
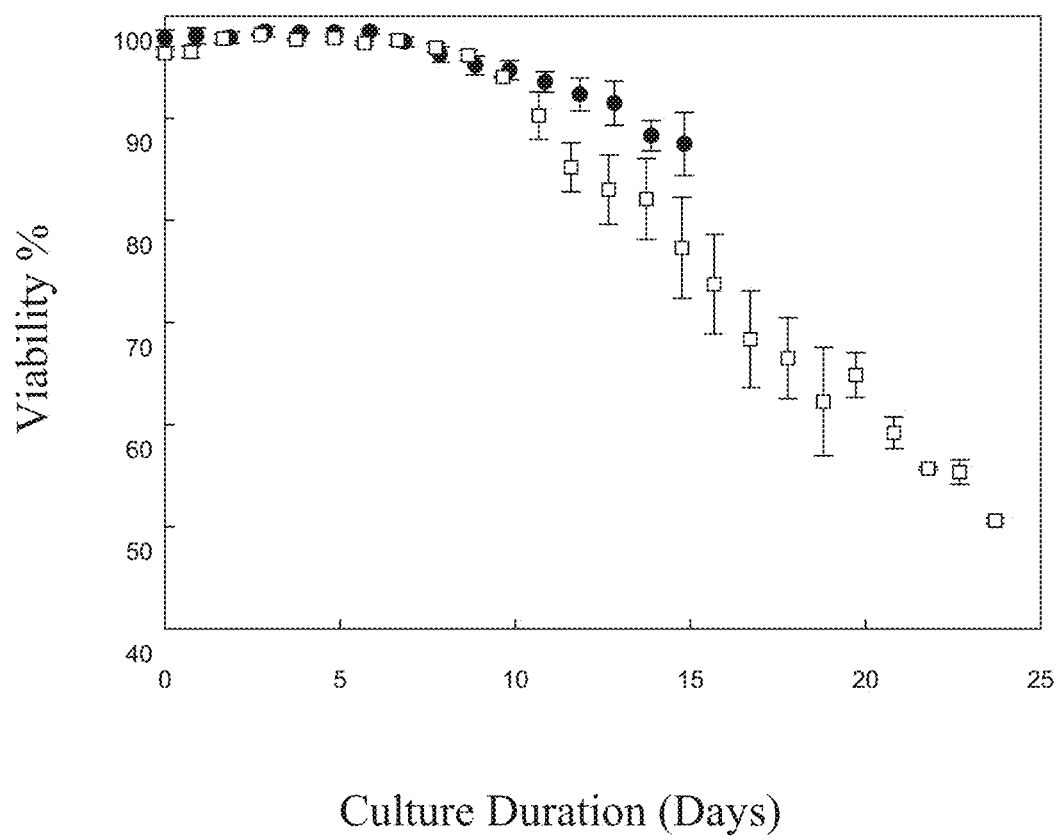
FIG. 4 Percent viability from extended periodic harvest process, n=2 (open square) compared to ultrafilter process, n=4 (closed circle).

The titer profile from the X-PH process was consistent with the titer from the UF culture process until day 11 (FIG. 2). The titer profiles separate when the first 750 kDa harvest cycle is introduced in the X-PH process. A similar correspondence was observed in the viable cell density (FIG. 3) and % viability FIG. 4).

A fifty-one day bioreactor production period was used to allow comparison of the X-PH process to the UF process with an allocated three day turnaround of the production bioreactor between runs. With this criterion, two 24 day X-PH process runs and three UF process runs would be done in a comparable fifty-one day period.

The X-PH process would provide 98% more recovered product compared to the UF process over a 51 day production period (Table 2). This mainly comprised a 26% increase in integrated viable cell density (IVCD) and a 46% increase in specific productivity. The X-PH process would use 27% more medium in two runs relative to three runs of the UF process, but this translates to a ~36% reduction of the medium requirement (medium cost) per gram of product produced by the X-PH process compared to the UF process.

TABLE 2

Product recovered over a 51 day Manufacturing Period in a 2 L bioreactor with 1.5 L working volume

| Process | Runs in 51 Days | IVCD ($\times 10^6$ cell-day/mL) | Specific Productivity (pg/cell-day) | Total Product Made (g) | Recovered Product PX-MF Harvest Bags (g) | Bioreactor Harvest (g) | Total Product Recovered (g) |
|---|---|---|---|---|---|---|---|
| UF | Single Run | 689.9 | ~27.9 | 28.9 | — | 23.1 | 23.1 |
|  | Three Runs | 2069.7 |  | 86.6 |  | 69.3 | 69.3 |
| X-PH | Single Run | 1302.8 | ~41.3 | 80.7 | 65.1 | 3.7 | 68.8 |
|  | Two Runs | 2605.6 |  | 161.3 | 130.2 | 7.3 | 137.5 |

The X-PH process product quality was evaluated by HILIC glycan mapping and compared to a standard generated using the 15 day UF process (Table 3). The X-PH process glycan map attributes are consistent with the standard using the UF process.

TABLE 3

| HILIC Glycan Analysis | | | | | |
|---|---|---|---|---|---|
| Process | | High Mannose (%) | Total Fucosylated (%) | Total Galactosylated (%) | Unknown (%) |
| X-PH | Harvest 1 Run #1 | 8.0 | 86.3 | 17.2 | 5.2 |
|  | Harvest 1 Run #2 | 9.5 | 84.3 | 18.4 | 5.7 |
|  | Harvest 2 Run #1 | 7.5 | 87.3 | 15.8 | 4.6 |
|  | Harvest 2 Run #2 | 7.9 | 86.5 | 16.1 | 4.9 |
|  | Harvest 3 Run #1 | 7.7 | 86.5 | 15.9 | 4.9 |
|  | Harvest 3 Run #2 | 8.3 | 85.8 | 15.0 | 4.9 |
|  | Harvest 4 Run #1 | 7.3 | 87.4 | 15.5 | 4.5 |
|  | Harvest 4 Run #2 | 7.8 | 86.6 | 14.9 | 4.9 |
|  | Harvest 5 Run #1 | 9.4 | 84.1 | 16.8 | 5.4 |
|  | Harvest 5 Run #2 | 8.9 | 84.5 | 14.8 | 5.5 |
|  | Mean ± Std Dev | 8.2 ± 0.8 | 85.9 ± 1.2 | 16.0 ± 1.1 | 5.1 + 0.4 |
| UF | Standard | 7.2 | 86.0 | 16.4 | 5.7 |

Example 2

This experiment compares the impact of low and high concentrations of the polyoxypropylene-polyoxyethylene block copolymer, (LUTROL® F68), and 30 kDa vs 750 kDa filters in a perfusion culture system.

On day 0, a CHO cell line expressing a recombinant antibody was inoculated into four 2 L bioreactors (Applikon Biotechnology, Foster City, Calif.) at $2\times10^6$ viable cells/mL in a working volume of 1500 ml of a serum-free chemically-defined perfusion medium containing 1 g/L polyoxypropylene-polyoxyethylene block copolymer (LUTROL® F68) (BASF, Mt Olive, N.J.). The cultures were maintained at 36° C., dissolved oxygen concentration at 48%, pH 6.9, agitation at 350 RPM.

The cell culture runs were initiated in batch mode: perfusion was started on day 2 when the cell densities reached $4\text{-}5\times10^6$ cells/ml. Perfusion was accomplished using an ATF-2™ alternating tangential flow perfusion and filtration system (Refine Technologies, Hanover, N.J.). The cell culture was continuously circulated through the lumen side of an external vertically oriented filter, entering at the upper end. Permeate was continuously withdrawn via peristaltic pump. Two reactors were equipped with 30 kDa hollow fiber filters (Xampler UFP-30-E-4MA, GE Healthcare, Pittsburgh, Pa.). Two reactors were equipped with 750 kDa hollow fiber filters (Xampler UFP-750-E-4MA, GE Healthcare, Pittsburgh, Pa.)

The perfusion rate increased gradually from 0.5 to 3 mL/minute over the cell culture run. Permeate samples were collected at the same rate as the perfusion rate. Samples were taken once daily from the bioreactor and the permeate line. Cell density, viability and cell diameter were measured by CEDEX (Roche. Nutley, N.J.) after dilution with phosphate-buffered saline to obtain a cell density of $<10^7$ cells/ml. The pH and partial pressure of CO2 ($pCO_2$) and $O_2$ ($pO_2$) were measured using a blood gas analyzer: concentration of glucose, lactate, glutamine, ammonia and ion concentrations of $K^+$ and $Na^+$ were maintained by a Nova-FLEX instrument (Nova Biomedical, Waltham, Mass.).

Figure 5:
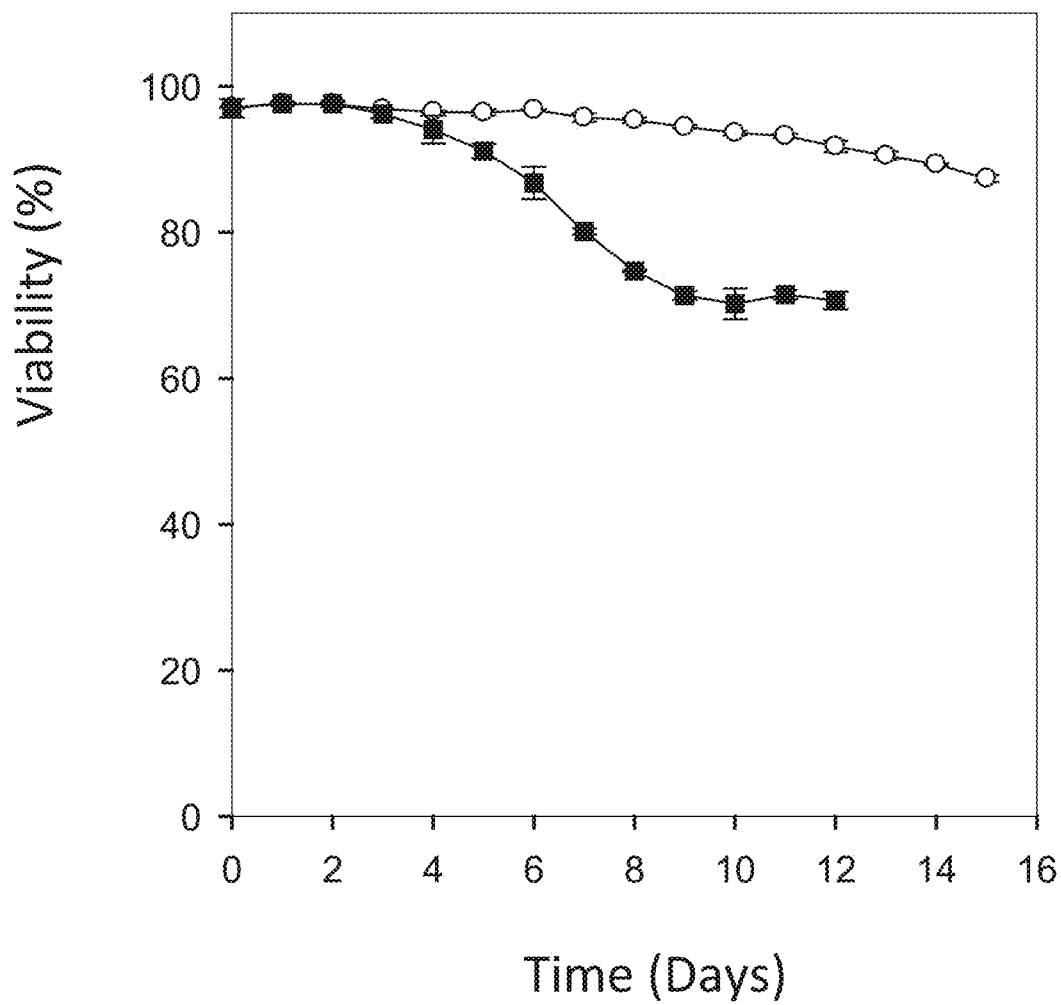
FIG. 5 Percent viability from reactors equipped with 750 kDa filter (open circles) and from reactors equipped with 30 kDa filters (closed circles). The percent viability decreased to 80% by day 6 in the reactors equipped with the 750 kDa filters. The percent viability in the reactors equipped with the 30 kDa filters was maintained at >80% for 14 days.

In reactors equipped with the 750 kDa filter, cellular viability decreased to 8(0% by Day 6. The decrease was not as pronounced in the reactors equipped with the 30 kDa filters in which viability was maintained at over 80% for 14 days. (FIG. 5)

Figure 6:
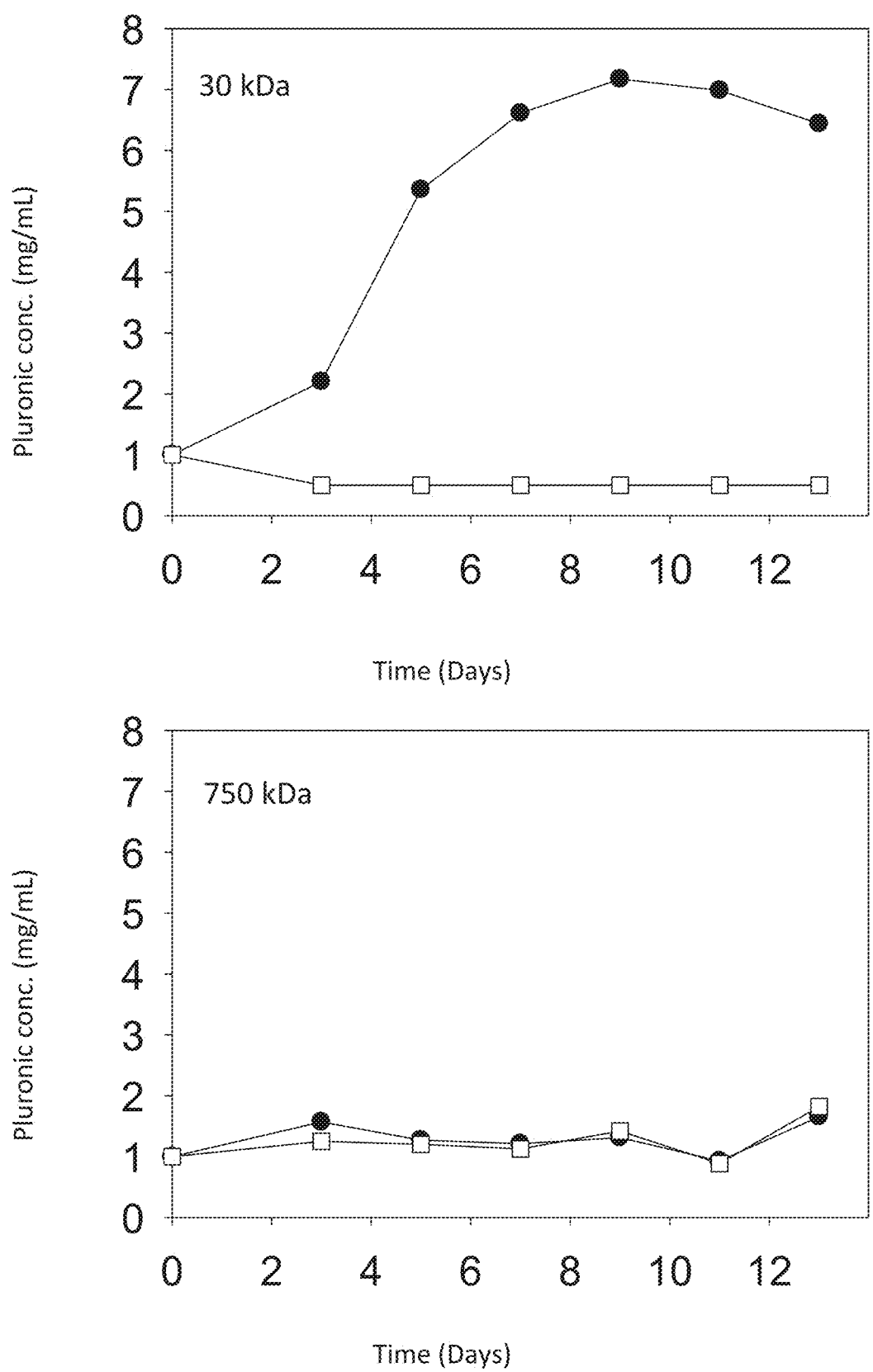
FIG. 6 Polyoxyethylene-polyoxypropylene block copolymer (LUTROL® F68) concentrations measured in the supernatant (closed circle) and the permeate (open square) of reactors with a 30 kDa or a 750 kDa hollow fiber filter unit. The 30 kDa supernatant shows an accumulation of polyoxyethylene-polyoxypropylene block copolymer (LUTROL® F68) over days 9-13.

Accumulation of up to 7 g/L of the polyoxypropylene-polyoxyethylene block copolymer (LUTROL® F68) in the supernatant of reactors equipped with the 30 kDa hollow fiber filter was seen. Under these conditions the polyoxypropylene-polyoxyethylene block copolymer (LUTROL® F68) was lower than detectable levels in the permeate samples In the reactors equipped with the 750 kDa filter, levels of the polyoxypropylene-polyoxyethylene block copolymer (LUTROL® F68) in the bioreactor supernatant and permeate remained relatively constant and similar to the levels in the perfusion medium, ranging from 1-1.5 g/L, suggesting no accumulation (FIG. 6). The average molar mass of the polyoxypropylene-polyoxyethylene block copolymer (LUTROL® F68) is 8,400 Da and theoretically should flow through the 30 kDa filter. Formation of polyoxypropylene-polyoxyethylene block copolymer (LUTROL® F68) micelles can occur at concentrations much lower than 1 g/L (0.04 mM at 20-25° C., according to the manufacturer). It is likely that the concentration of the polyoxypropylene-polyoxyethylene block copolymer (LUTROL® F68) was enhanced due to the formation of micelles within the reactor and the filter.

[Polyoxypropylene-polyoxyethylene block copolymer] [LUTROL]® F68 toxicity studies To test for the effect of toxicity of high polyoxypropylene-polyoxyethylene block copolymer (LUTROL® F68) concentration on cells, two CHO cell lines (Cell line A and Cell line B) expressing different monoclonal antibodies were carried over 10 passages (at 3 days/passage), at an initial seeding density of $8 \times 10^5$ cells/ml in 250 ml shake flasks with cell culture media containing 1, 2, 3, 4 or 5 g/L polyoxypropylene-polyoxyethylene block copolymer (LUTROL® F68).

An overall increase in cell density was observed (3.4-$6.5 \times 10^6$ cells/ml) after 3 days. Viable cell density was normalized to the 1 g/L condition to enable comparison between the different polyoxypropylene-polyoxyethylene block copolymer (LUTROL® F68) concentrations.

Figure 7A:
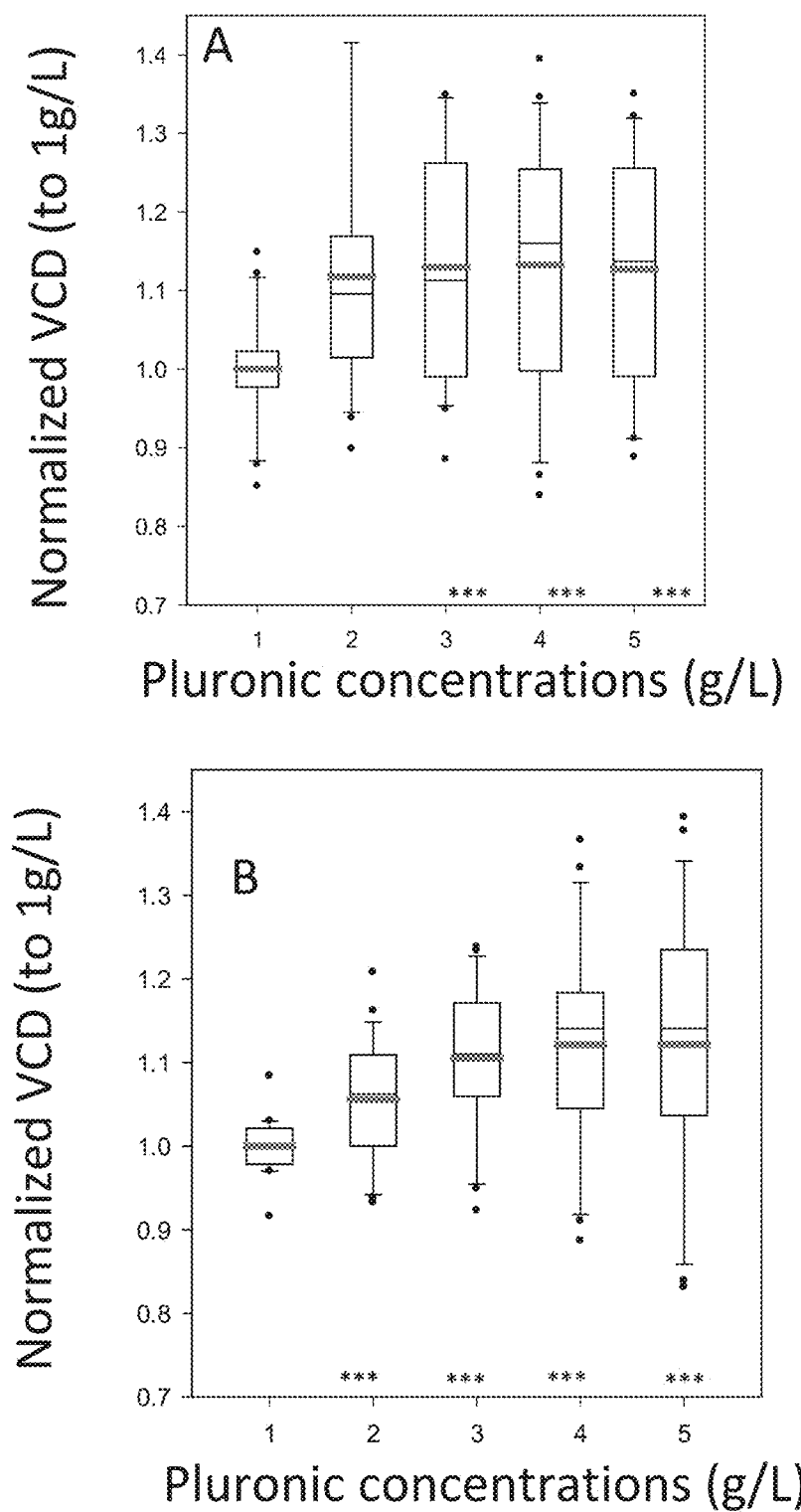
FIG. 7A Normalized viable cell density for cell lines A and B at each polyoxyethylene-polyoxypropylene block copolymer (LUTROL® F68) concentration (2 g/L-5 g/L) compared to 1 g/L, giving cell density ratio. Comparisons were made using Student's t-tests between the data at all passages compared to that of 1 g/L. Statistical significance: * ≤0.0001;  ≤0.001; * ≤0.01; **** ≤0.05.
Figure 7B:
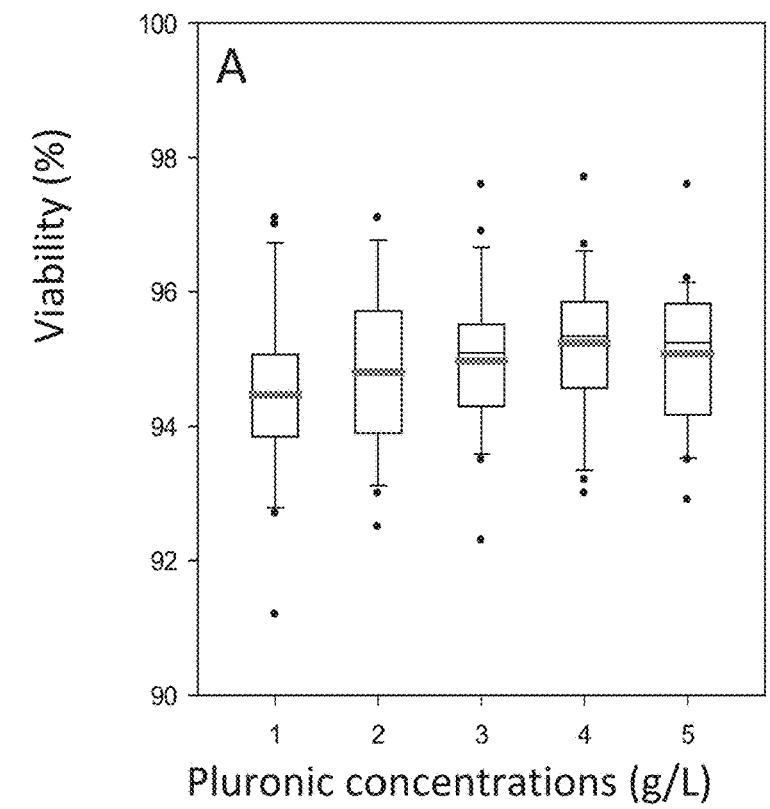
FIG. 7B Percent viability for cell lines A and B at each polyoxyethylene-polyoxypropylene block copolymer (LUTROL® F68) concentration (2 g/L-5 g/L) compared to 1 g/L. Comparisons were made using Student's t-tests between the data at all passages compared to that of 1 g/L. Statistical significance: * ≤0.0001;  ≤0.001; * ≤0.01; **** ≤0.05.
Figure 7B:
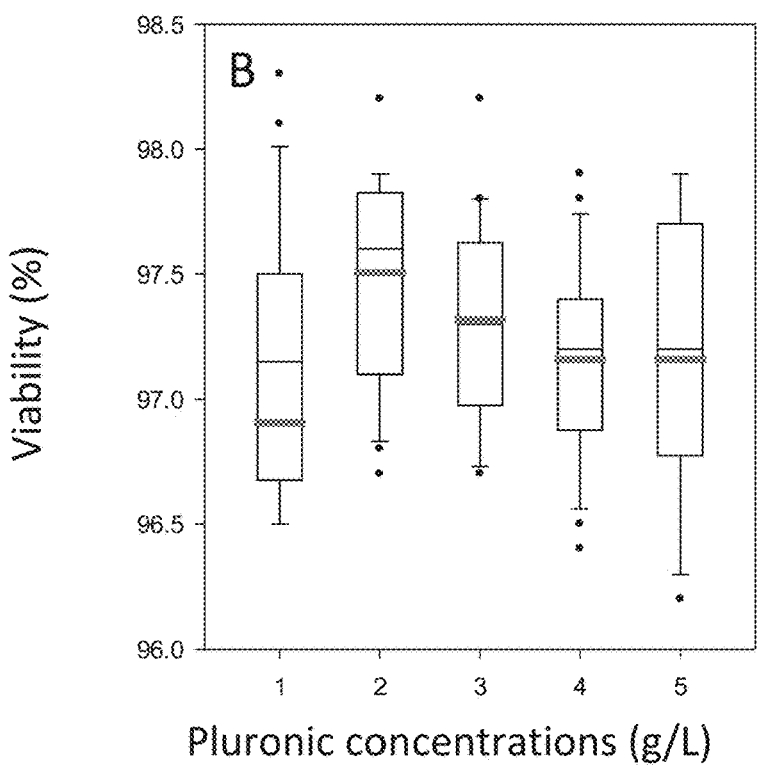
Figure 7C:
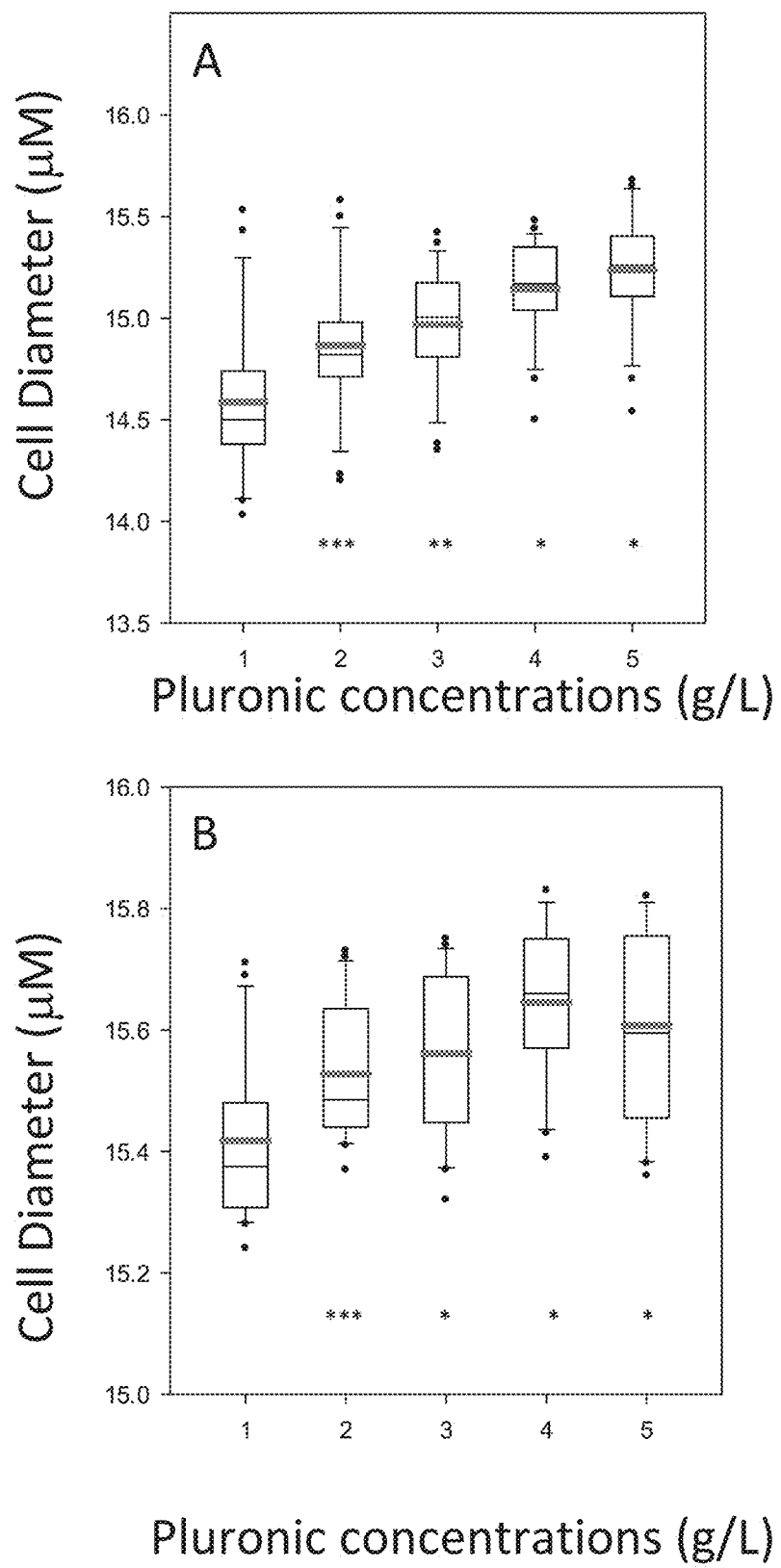
FIG. 7C Cell diameter for cell lines A and B at each polyoxyethylene-polyoxypropylene block copolymer (LUTROL® F68) concentration compared to the cell diameter at 1 g/L polyoxyethylene-polyoxypropylene block copolymer (LUTROL® F68). Comparisons were made using Student's t-tests between the data at all passages compared to that of 1 g/L. Statistical significance: * ≤0.0001;  ≤0.001; * ≤0.01; **** ≤0.05.

The cells grown in media containing 3, 4 or 5 g/L polyoxypropylene-polyoxyethylene block copolymer (LUTROL® F68) were consistently higher over the passages, in which a 10% increase in cell density was measured compared to the 1 g/L condition ($p<0.01$) (FIG. 7A). The viability was also greater for the higher polyoxypropylene-polyoxyethylene block copolymer (LUTROL® F68) cultures (mean >95%) (FIG. 7B). Cell diameter was also found to have increased slightly in all conditions compared to the 1 g/L condition (15.42 µM) ($p<0.05$) (FIG. 7C). The variation of viable cell density, % viability.

Figure 8:
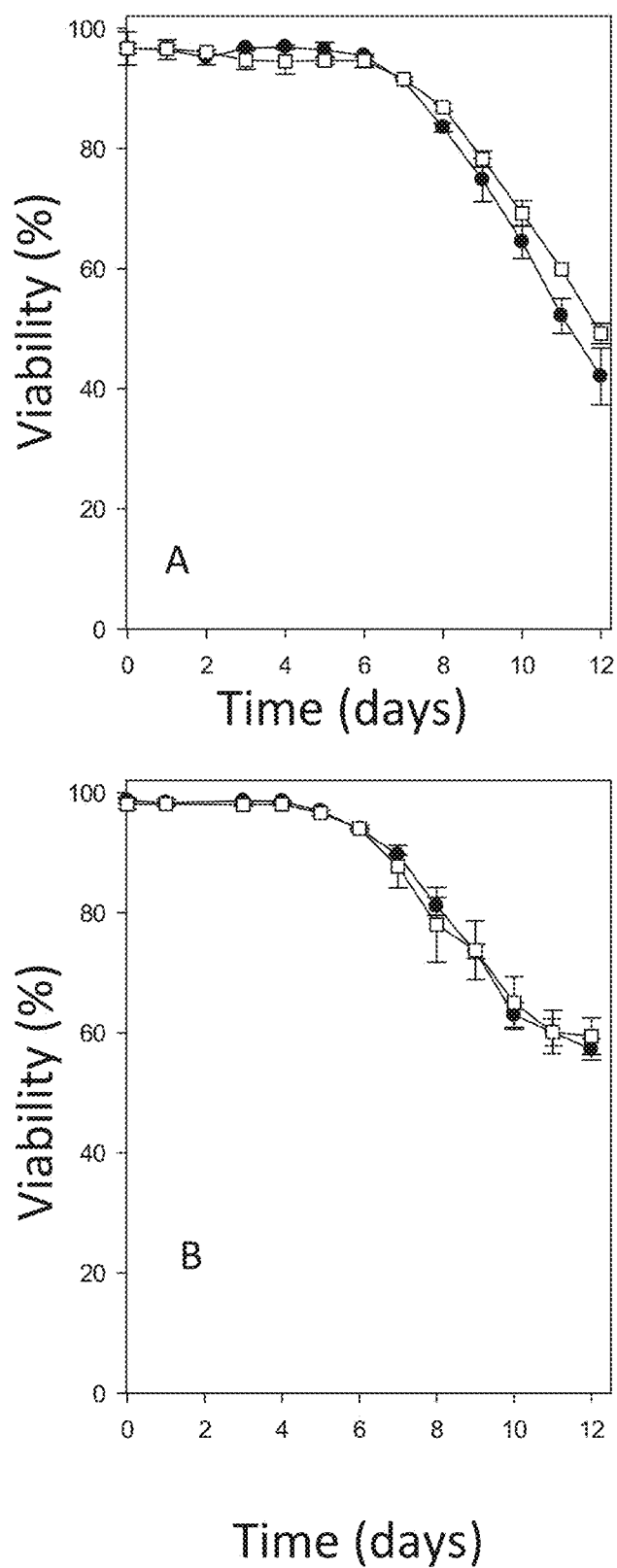
FIG. 8 Percent cell viability for cell lines A and B at 1 g/L polyoxyethylene-polyoxypropylene block copolymer (LUTROL® F68) (open squares) and 5 g/L polyoxyethylene-polyoxypropylene block copolymer (LUTROL® F68) (closed circles). Viability was maintained at >90% for >30 days when concentration of polyoxyethylene-polyoxypropylene block copolymer (LUTROL® F68) was increased to 5 g/L.

The effect of toxicity of high polyoxypropylene-polyoxyethylene block copolymer (LUTROL® F68) concentration on cells was also carried out in a 2 L fed-batch culture using two CHO cell lines expressing monoclonal antibodies. Again, there was no impact of the high polyoxypropylene-polyoxyethylene block copolymer (LUTROL® F68) on viable cell density, viability, cell diameter or titer (FIG. 8).

Supplementing ATF alternating tangential flow perfusion cultures with 5 g/L [polyoxypropylene-polyoxyethylene block copolymer] [LUTROL]® F68

An experiment comparing 1 g/L and 5 g/L polyoxypropylene-polyoxyethylene block copolymer (LUTROL® F68) was performed. On day 0, a CHO cell line expressing a recombinant antibody was inoculated into six 2 L bioreactors (Applikon Biotechnology, Foster City, Calif.) at $2 \times 10^6$ viable cells/mL in a working volume of 1500 ml. Two reactors received a serum-free defined perfusion medium containing 1 g/L polyoxypropylene-polyoxyethylene block copolymer (LUTROL® F68) and two reactors received a serum-free defined perfusion medium containing 5 g/L polyoxypropylene-polyoxyethylene block copolymer (LUTROL® F68). The cultures were maintained at 36° C., dissolved oxygen concentration at 48%, pH 6.9, agitation at 350 RPM.

The cell culture runs were initiated in batch mode; perfusion was started on day 2. Perfusion was accomplished using an ATF-2™ alternating tangential flow filtration system (Refine Technologies, Hanover, N.J.) equipped with 750 kDa hollow fiber filters (XAMPLER UFP-750-E-4MA, GE Healthcare, Pittsburgh, Pa.). The perfusion rate was 3 working volumes/day.

Samples were taken once daily from the bioreactor and the permeate line and were tested as described above.

Figure 9:
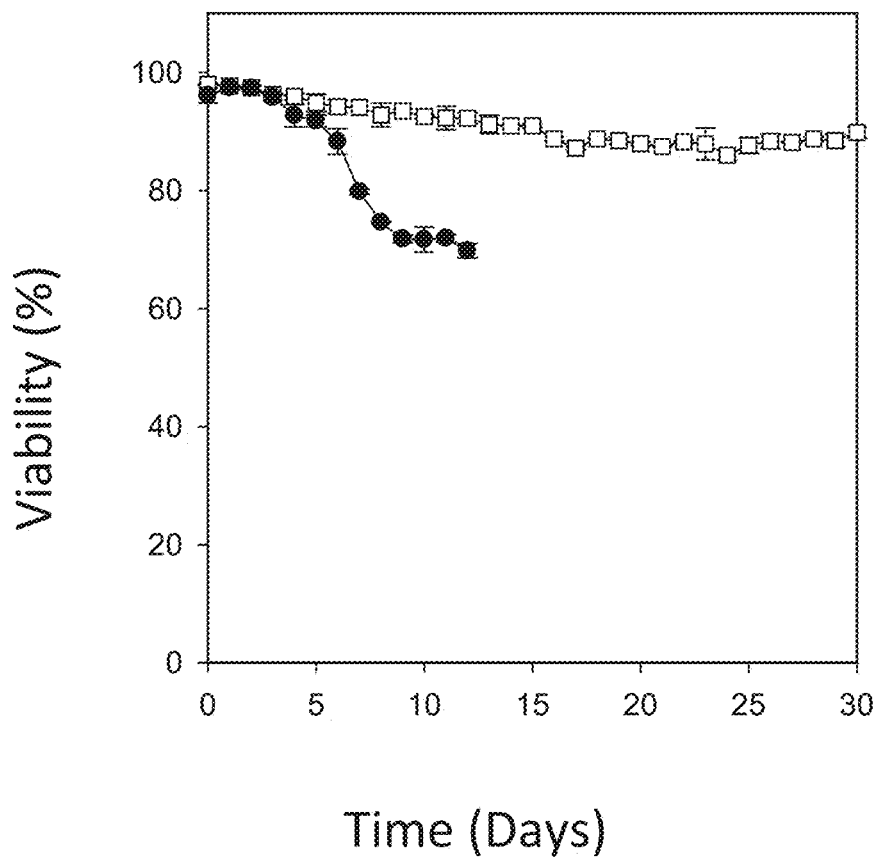
FIG. 9 The effect of pluronic concentration on the viability of cells grown in 2 L reactors with a 750 kDa filter for ATF® alternating tangential flow, with perfusion media containing 1 g/L polyoxyethylene-polyoxypropylene block copolymer (LUTROL® F68) (closed square) or 5 g/L polyoxyethylene-polyoxypropylene block copolymer (LUTROL® F68) (open circle).

Increasing the polyoxypropylene-polyoxyethylene block copolymer (LUTROL® F68) concentration to 5 g/L resulted in extended viability of >95% for 14 days and >90% for up to day 25 (FIG. 9).

Recovery of low [polyoxypropylene-polyoxyethylene block copolymer] [LUTROL]® F68 concentration cultures with high [polyoxypropylene-polyoxyethylene block copolymer] [LUTROL]® F68

Figure 10:
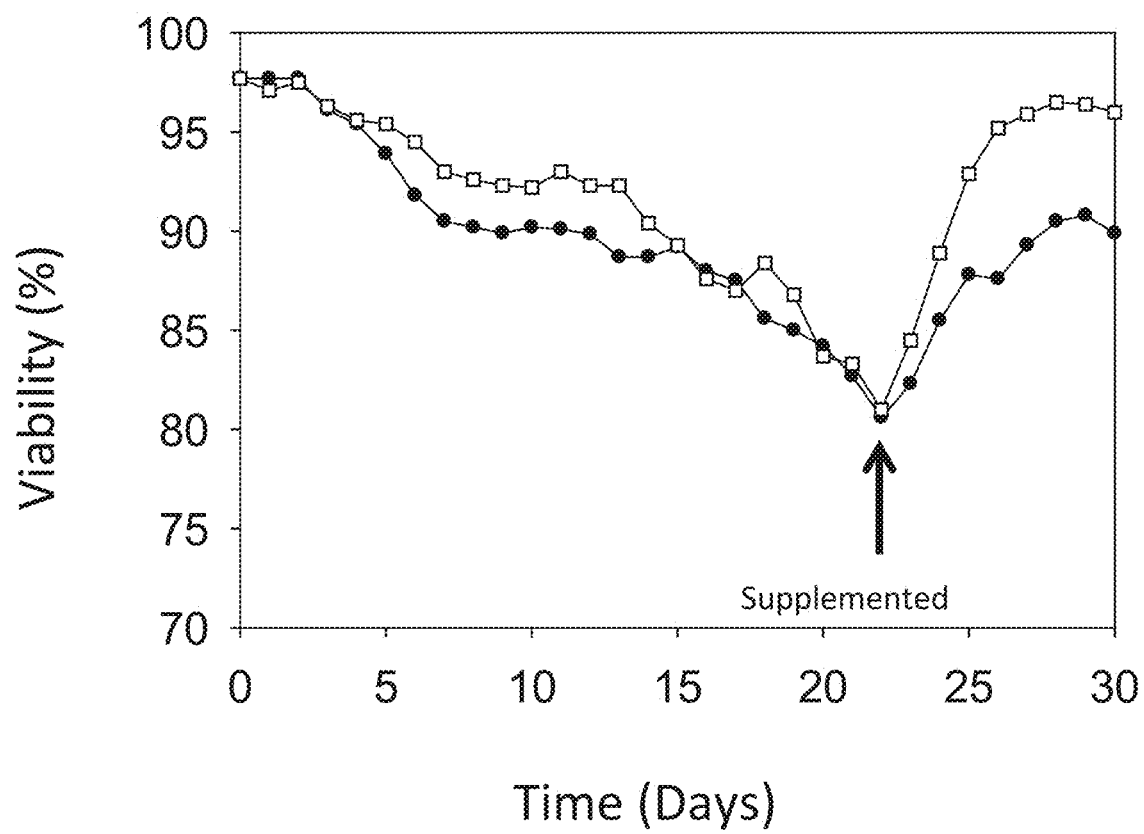
FIG. 10 The effect of increasing the concentration of polyoxyethylene-polyoxypropylene block copolymer (LUTROL® F68) (up to 5 g/L) on the recovery of viability of cells growing at 1 g/L polyoxyethylene-polyoxypropylene block copolymer (LUTROL® F68) in 2 L reactors with a 750 kDa filter for ATF® alternating tangential flow. Media A: closed circle. Media B: open circle. Arrow indicates when polyoxyethylene-polyoxypropylene block copolymer (LUTROL® F68) concentration was increased.

On day 0, a CHO cell line expressing a recombinant antibody was inoculated into four 2 L production bioreactors (Applikon Biotechnology, Foster City, Calif.) at $2 \times 10^6$ cells/mL in a working volume of 1500 ml. The cell culture runs were initiated in batch mode; perfusion was started on day 2. Perfusion was accomplished using an ATF-2™ alternating tangential flow filtration system (Refine Technologies, Hanover, N.J.) equipped with 750 kDa hollow fiber filters (XAMPLER™ UFP-750-E-4MA, GE Healthcare, Pittsburgh, Pa.). The reactors were divided into two groups of two, each group receiving a different perfusion cell culture medium formulation (Media A and Media B). Both media formulations contained 1 g/L polyoxypropylene-polyoxyethylene block copolymer (LUTROL® F68). The cultures were maintained at 36° C., dissolved oxygen concentration at 48%, pH 6.9, agitation at 350 RPM. The cultures were maintained under these conditions until the percent cell viability dropped to 80%. At that time, the media for both groups was supplemented with an additional 4 g/L polyoxypropylene-polyoxyethylene block copolymer (LUTROL® F68) (for a total of 5 g/L). The cultures were maintained under these high pluronic conditions until day 30. Recovery of cellular viability by addition of a higher concentration of polyoxypropylene-polyoxyethylene block copolymer (LUTROL® F68) is shown in FIG. 10. After supplementation, the percent viability increased by up to 15%. The protective effect of the higher concentration of pluronic in a culture with declining cell viability was evident regardless of the cell culture media formulation.

Example 3

This experiment demonstrates the successful pilot scale application of multiple quality by design (QbD) elements into a PAC process to deliver a predefined quality target product profile (QTPP). The controlled CQA in this experiment was high-mannose N-linked glycosylation on the Fc-domain of a monoclonal antibody ("high mannose").

The level of high mannose in the product was controlled by addition or removal of mannose (the control lever) to the cell-culture media. However, metabolite precursors, metabolic inhibitors, small molecules, enzymatic cofactors and inducible promoters could also be used. Recent studies have shown that different sugars can impact the level of high mannose on an antibody product. Specifically the feeding of mannose has been shown to increase the level of high mannose without impacting culture productivity. Through empirical studies, an understanding of the impact of mannose concentration in the cell culture media on IgG high mannose levels was developed and the relationship to the cell culture process was studied. The knowledge gained from small-scale studies and a training production run at pilot scale was incorporated to develop a PAC algorithm based on the principle of Model Predictive Control (MPC). MPC is a control scheme in which a mathematical model of the process is used to predict its future trajectory. The transient nature of a typical CHO bioreactor processes, the likelihood of interactions between multiple CQAs and their control levers, and the lags associated with complex analytics all provide strong motivation for MPC. PAT technologies including near real-time mass spectrometry analytics combined with standard bioreactor monitoring were used to provide timely data to inform the model used for MPC. Data from the multiple assays were incorporated into the MPC system which determined the amount of mannose to add to the bioreactor to maintain the high mannose CQA within the target range.

Cell Culture Plate Assay Ratios of Glucose to Mannose:

The cell line was a recombinant CHO cell line expressing a monoclonal antibody. The cells were seeded at 7.5e5 cells/mL in chemically defined (CD) medium containing 12 g/L glucose at a working volume of 2 mL in deep-well plates. The cells were incubated in an orbital shaker at 36.0° C. and 5% $CO_2$ at 220 rpm (orbital diameter of 50 mm). On days 3-4, the glucose concentration was measured via a Polychem Glucose Reagent Plate Assay (MedTest DX, Canton Mich.) and the cultures centrifuged to replace 26% of the spent medium with fresh CD medium. Similarly, on day 5, 100% of the spent medium was replaced with fresh CD medium that contained no glucose. The total hexose concentration was subsequently adjusted to 10 g/L using different ratios of glucose to mannose by addition from concentrated hexose stock solutions. Cells were allowed to grow for 24 hours. Supernatants were removed, IgG was purified and % high mannose was measured by a hydrophilic interaction liquid chromatography (HILIC) assay.

GC-MS Hexose Assay

Glucose and mannose concentrations were quantified in cell culture media by GC-MS. A 1 mL sample of cell culture was centrifuged to pellet cells and the supernatant was filtered (0.2 μM). The filtered supernatant was diluted 1 in 10 into DI water and 10 μL of this dilution added to a 1.5 μL centrifuge tube. A 5 μL aliquot of a hexose internal standard solution was added containing 10 mM D-[UL-13C6]mannose 99.9% (Omicron Biochemicals) and 10 mM D-[U-13C6]glucose 99.9% (Cambridge Isotope Labs). The sample was dried (SpeedVac) for 30 min. Hexoses were derivatized by the addition of 20 μL anhydrous pyridine and 30 μL of N-methyl-N-(trimethylsilyl)trifluoroacetamide (MSTFA) with 1% trimethychlorosilane (TMCS) incubated at 40° C. for 30 min. Immediately after derivatization, samples were analyzed on an Agilent GC 6890N MSD 5973 system. A 1 μL sample was injected on an Agilent DB-35 GC column (30 m×0.32 mm×0.25 um) with a 1 in 50 split. Helium was held at a constant flow of 1 mL/min. Oven temperature was held at 190'C for 2 min and ramped up to 202° C. at a rate of 4° C./min.

Figure 11:
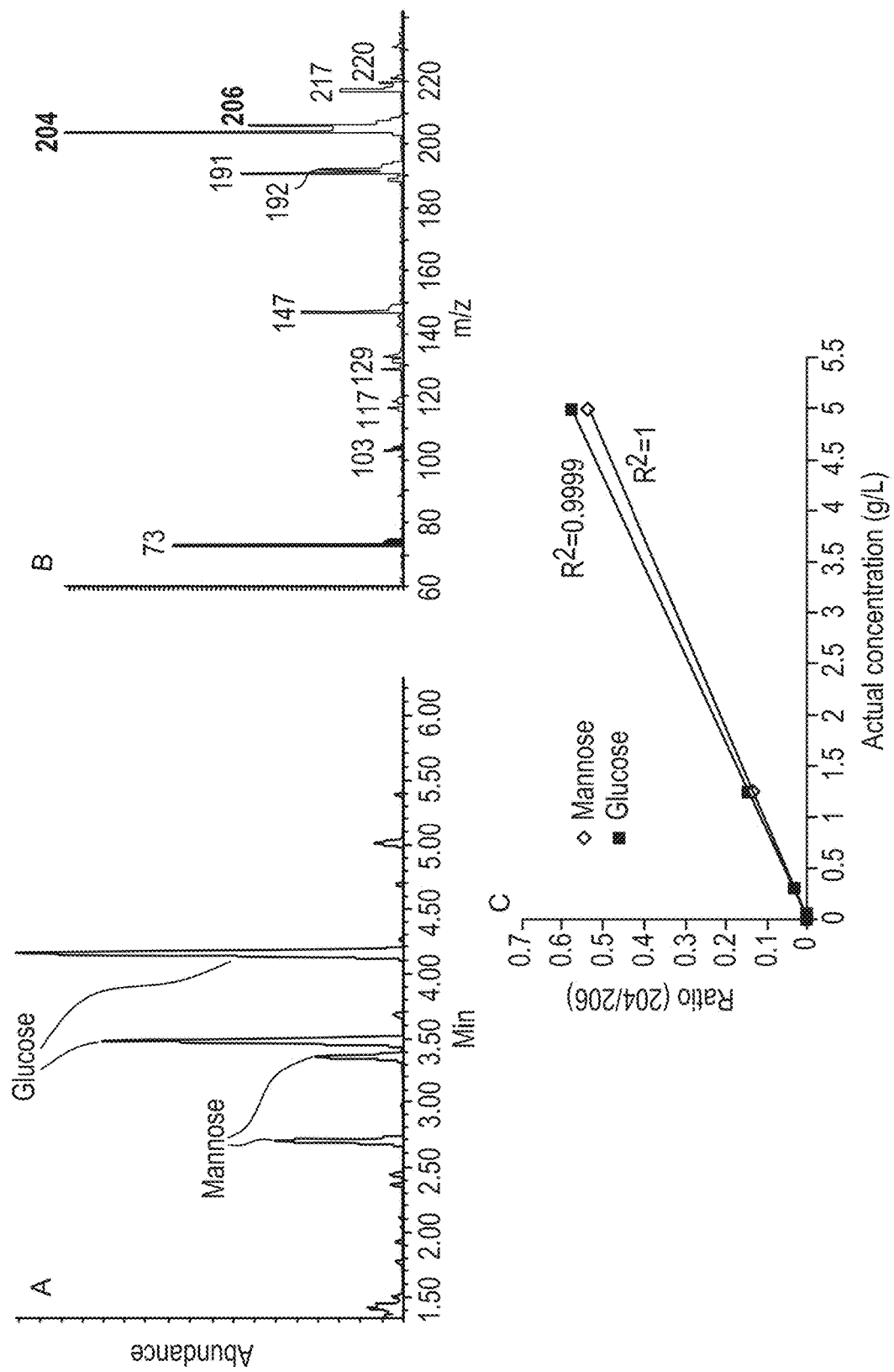
FIG. 11: GCMS quantification of glucose and mannose. (A) TIC for GC separation of hexoses and (B) typical mass spectrum fragmentation pattern found in hexose peaks containing both the 12C-hexose and 13C-internal standard hexose. (C) Assay linearity for glucose and mannose quantification.

Temperature was further ramped to 280° C. at a rate of 60° C./min. Total run time was 6.3 min. Each hexose gave two peaks representing both open and closed isomeric forms. Mannose eluted at 2.7 min and 3.34 min; glucose eluted at 3.5 min and 4.18 min (FIG. 11(A)). The 3.34 min peak area was used for mannose quantification and the 4.18 min peak for glucose quantification. Hexoses were quantified using the characteristic TMS carbohydrate fragment m/z=20416 and standard isotope dilution where the m/z=204 peak area of the 12C sugar was compared to the m/z=206 peak area of the 13C sugar (FIG. 11 (B)).

IdeS [Enzyme] [FABRICATOR®] Limited Proteolysis MS-PAT Assay

Filtered cell-culture media samples were analyzed without further purification. Approximately 60 μg of each sample were digested with 60 units of IdeS enzyme (FABRICATOR®, Genovis, Lund, Sweden) at 37° C. for 30 minutes. The digested samples were then reduced in 4M guanidine hydrochloride with 50 mM Dithiothreitol (DTT) at 55° C. for 10 minutes. Then, the digested and reduced samples were analyzed by RP-HPLC/MS.

RP-HPLC/MS analysis was performed using Waters Acquity Ultra-Performance liquid chromatography (UPLC) (Milford, Mass.) coupled to an Agilent MST Time of Flight (TOF) mass spectrometer (Santa Clara, Calif.). The prepared samples were separated on a reversed-phased Waters BEH phenyl column (1.7 μm, 2.1×150 mm; Milford, Mass.) maintained at 80° C. The peaks were monitored by UV at 220 nm and TOF-MS. The mass data were extracted from the total ion current (TIC) of the peaks, followed by deconvolution and quantification using Agilent MassHunter software.

Hydrophilic Interaction Chromatography (HILIC) Glycan Map Assay

100 μg of purified antibody was digested with PNGase F (New England Biolabs) followed by addition of 50 μL fluorescent labeling solution containing 12 mg/mL 2-aminobenzoic acid (2AA) with 0.04 M sodium cyanoborohydride. This mixture was incubated at 80° C. for 75 minutes. The labeled glycans were analyzed by Acquity UPLC equipped with a Fluorescence Detector (Milford, Mass.). Approximately 3 μL of labeled glycans was injected to an Acquity UPLC BEH Glycan Column (#186004741, Milford, Mass.) followed by fluorescence detector using an emission at 360 nm and detection at 425 nm. The 2AA labeled glycan species were identified by MS/MS technique.

The generation of data for fitting the model parameters, and the subsequent demonstration of MPC for control of % high mannose were performed in bioreactors. Mannose (Sigma, M6020) was added on the first day of culture to a culture concentration of 1 g/L using a 25% stock solution. Perfusion was initiated on culture day two. Perfusion media was delivered at increasing volumes from 0.5 to 1.0 bioreactor volumes per day. The bioreactor was controlled using Delta V automation (Emerson). Bioreactor sampling was performed every four hours using the MAST SP200 autosample valve (Bend Research) for titer, hexose and product glycan measurement. After automated sample collection, samples were manually centrifuged and 0.2 um filtered to remove cells and debris. Daily samples for measurements of growth, viability, osmolality, and lactate were collected either manually or using the MAST SP200. Viable cell density (VCD) and culture % viability were measured using a Nova CDV (Nova Biomedical). Lactate concentrations were determined using a Nova Bioprofile Basic analyzer (Nova Biomedical).

Model Predictive Control

Programming for the Model Predictive Control (MPC) and for fitting model parameters was done in MATLAB (version R2014a, Mathworks) and the code is available in the supplemental materials. The model parameters were determined by least squares regression of the model equations to data from a single training reactor run. For control of high mannose by mannose feeds (via MPC) each daily rate change was calculated via the following steps.

1. Calculation of current model offset. The reactor operational history combined with daily measured values (if available) were used as inputs to generate a numerical solution of the model differential equations. The difference between the model and the most recent measurement could then be calculated. This difference was used as an estimate of the future offset.

$H_k$—Model value at timepoint k=$f(t_k)$
$H'_k$=Measured value at timepoint k
$H_{k+1}$=Adjusted predicted value at timepoint k+1=$F(t_{k+1})$+$(H_k-H'_k)$ 2. Determination of optimal future rates via MPC. The standard MPC receding horizon method17 was used on each day once the control was initiated. The optimal set of five rate changes was determined by minimizing sum of the squared error between the product quality profile predicted by the model and the target setpoint. Although five rate changes were calculated, only the first one was used. By the time the next rate change was due to be implemented, new data were available which were then used to recalculate the optimal set of future rates.

The mannose feed rate was found by treating it as the independent variable in the minimization of the objective function (which in this case is the sum of squares of the difference between the desired high mannose level on the molecule and that found via integration of the governing differential equations). The above equations are sufficiently well behaved so the solution obtained by the MATLAB solvers was sufficient for control to +/−1% high mannose species on the antibody. The method for controlling high mannose is one sided in that addition of mannose to the reactor increases % high mannose on the antibody. The reduction of % high mannose production is achieved by reducing the mannose concentration (by dilution via perfusion after lowering the mannose feed rate).

GC-MS Hexose Quantification

Real-time quantification of mannose was a necessary input for MPC. GCMS was used to distinguish the hexoses (mannose and glucose) in cell culture media. Hexoses were quantified by isotope dilution as described above. FIG. 11(A) shows baseline separation by GC of mannose and from cell culture media during a typical run. FIG. 11(B) shows the hexose fragmentation pattern (identical between mannose and glucose), where the m/z 204 peak was quantified using the m/z 206 peak from the 13C labeled internal standard. The limit of detection for both glucose and mannose was 0.02 g/L and linearity was demonstrated for quantification up to 6 g/L hexose (FIG. 11(C)).

Cell Culture Plate Assay Ratios of Glucose to Mannose

Figure 12:
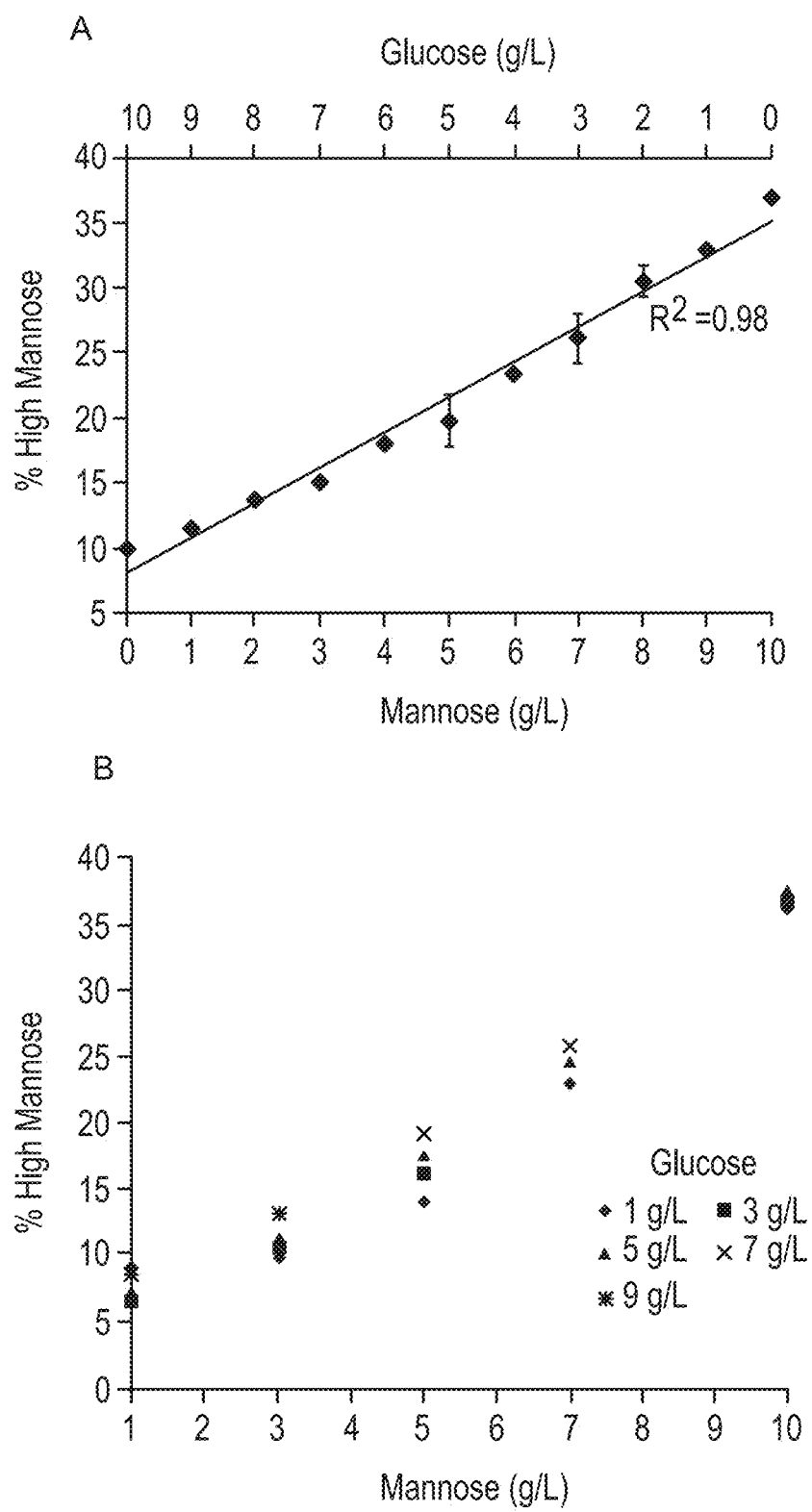
FIG. 12: The effect of mannose on high mannose glycosylation of IgG. (A) CHO cells cultured with increasing amounts of mannose; (B) CHO cells cultured with increasing amounts of mannose and at different concentrations of glucose. The linear increase in high mannose glycosylation is independent of glucose concentration.

Cells were cultured with a constant 10 g/L total hexose but increasing the concentration of mannose to give the glucose:mannose ratios of 10:0, 9:1, 8:2, 7:3, 6:4, 5:5, 4:6, 3:7, 2:8 and 0:10. Cells were cultured for 24 hours with the different hexose ratios. Supernatants were removed, IgG was purified and % high mannose was measured by HILIC assay. FIG. 12(A) demonstrates a linear relationship between the concentration of mannose in the cell culture media and the total high mannose level, where high mannose was lowest at 10% in media containing only glucose and highest at 37% in media containing only mannose.

To establish if the increase in high mannose was due to either the increase in mannose sugar concentration or the decrease in glucose sugar concentration, cells were cultured as for the first plate experiment, with the exception of day 5, where media was exchanged for fresh media containing 1, 3, 5, 7 or 10 g/L mannose. Five different concentrations of glucose (1, 3, 5, 7 or 9 g/L) were added to each of the mannose containing cultures. This made for a total of 25 different cultures with the lowest amount of total hexose being 2 g/L (1 gm/L glucose and 1 gm/L mannose FIG. 12(B)) and the highest 19 g/L (9 gm/L glucose and 10 gm/L mannose; FIG. 12(B)). Cells were allowed to grow for 24 hours. Supernatants were then removed, IgG was purified and % high mannose was measured by HILIC assay. FIG. 12(B) indicates that the linear increase in high mannose is independent of glucose concentration and only dependent on mannose concentration in the media. This relationship was used to develop a MPC control loop.

Control Loop Development: Model Predictive Control

Figure 13:
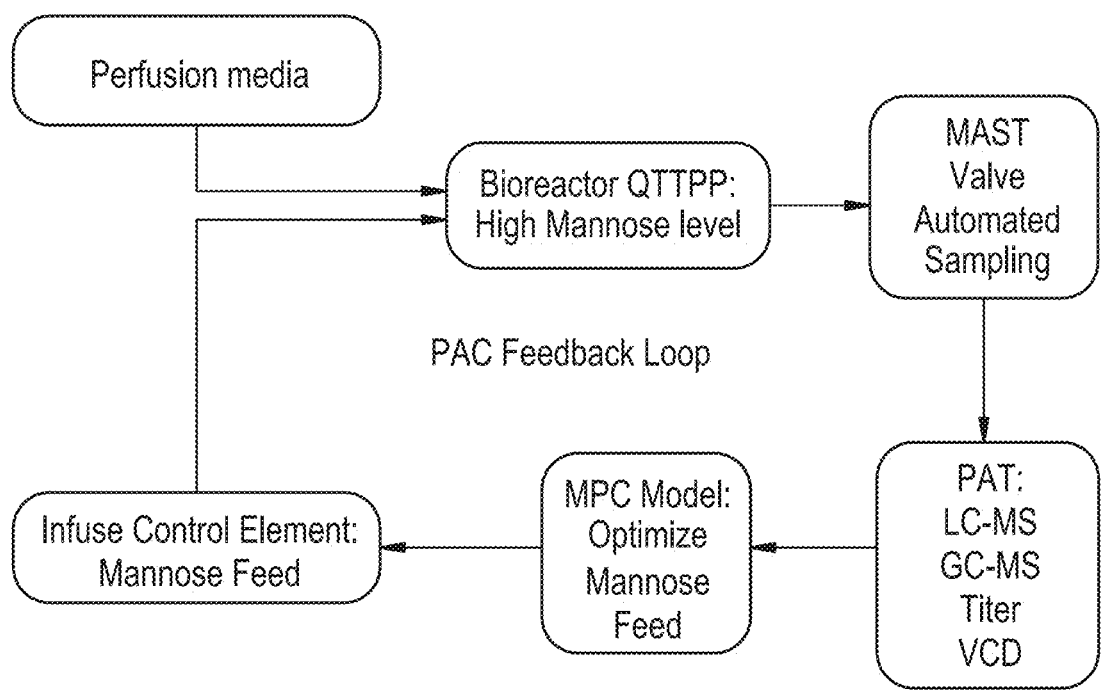
FIG. 13: Schematic of the PAC feedback loop. The key elements of the PAC process needed to deliver predefined product quality attributes are the QTPP, a PAT system including automated sampling and attribute specific analytics, a control model to modify the process and a process with known control levers to adjust attribute levels.
Figure 14:
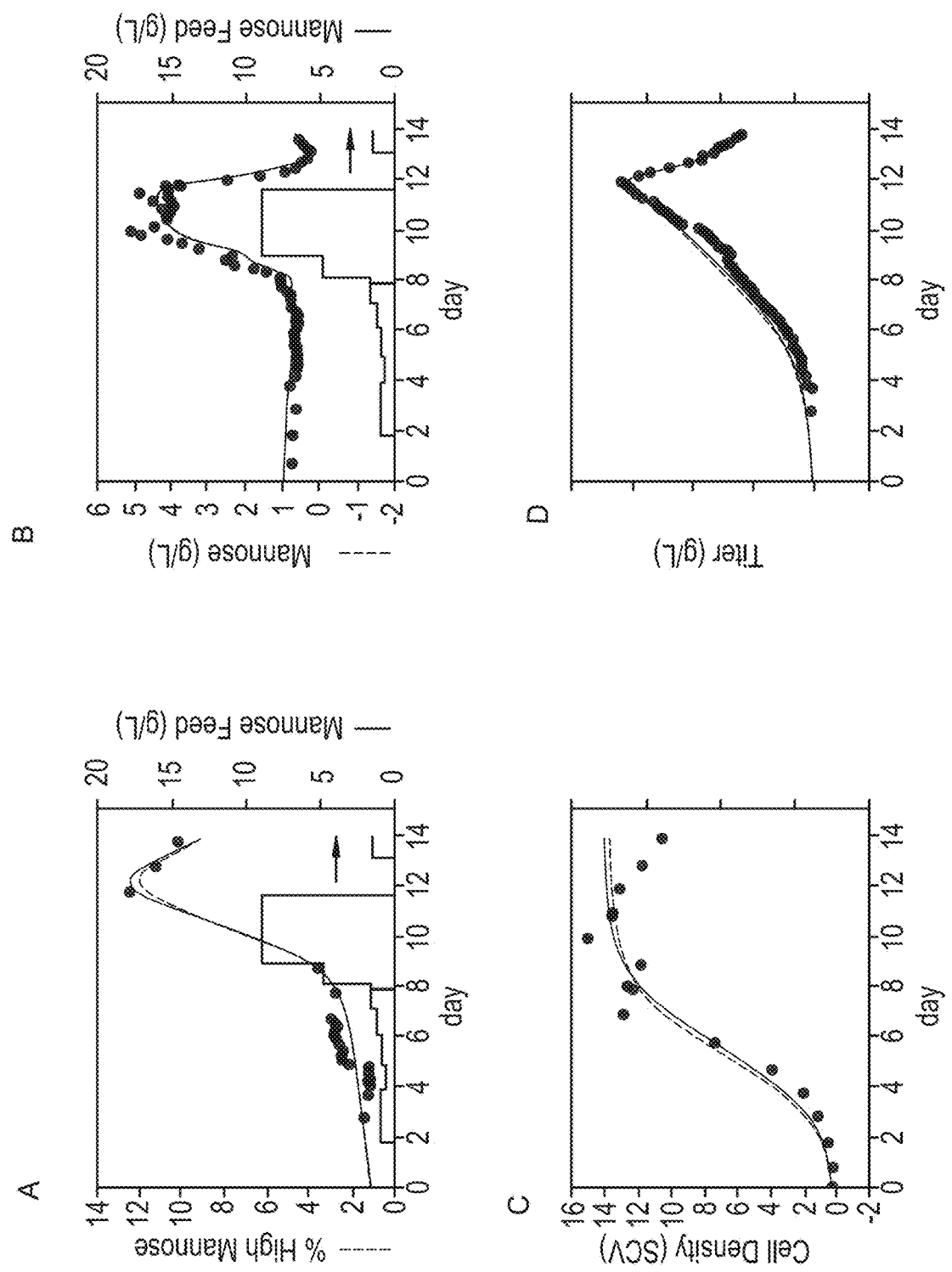
FIG. 14. A single reactor run was used to calculate model parameters via least squares regression. The symbols are the measurements used to find the model parameters via least squares regression. The dashed lines are the resulting model outputs. The dotted lines are the model fits using the growth parameters which were used for MPC. The solid red lines in figures A and B show the mannose feed used to generate this training data. A) % high mannose B) Reactor mannose concentration C) Cell density (arbitrarily scaled calculated volume) D) Product concentration

For control loop development, the bioreactor was connected to the MAST SP200 automated sampling device and a mannose solution feed pump in addition to routine bioreactor controls and off-line analytics (FIG. 13). A 15 day perfusion bioreactor run was performed to generate training data to develop the MPC feedback loop for one sided control of high mannose using mannose feeds. Data for % high mannose (FIG. 14(A)), mannose concentration in the reactor (FIG. 14(B)), cell growth (FIG. 14(C)) and titer accumulation (FIG. 14(D)) were collected at 4 hour time intervals with the exception of glycan data which was not collected during days 9-11. The MPC model was developed from this data set, except for the growth parameters which, due to an error, were calculated from a similar run. The model predictions using both sets of growth parameters are shown in FIG. 14 and are virtually identical.

Control Loop Development: Model Equations

Ordinary differential equations were constructed to describe the rate of change of cell number, product, mannose concentration, and high mannose species.

$$\frac{dN}{dt} = \frac{\mu N(N_m - N)}{N_m}$$

Here N is the cell density, p is the maximum growth rate, and Nm is the maximum cell density. The cell density can be in cells/volume or cell volume/volume. In this work a calculated and arbitrarily scaled volume was calculated from cell count and diameter measured on the Nova CDV. For titer, the specific productivity was assumed to be constant and variable retention of product (which depends on the perfusion filter used) is accounted for:

$$\frac{dP}{dt} = q_P N - SDP$$

The product concentration is P, and $q_p$ is the specific productivity. S is the sieving coefficient which is the fraction of product which passes through the perfusion filter, and D is the perfusion rate in reactor volumes/day. The rate of change of mannose $$\frac{dM}{dt} = D(M_f - M) - q_M N$$

Mannose concentration in the reactor is M, $M_f$ is the effective concentration of mannose in the perfusion medium and $q_M$ is the specific mannose consumption rate. Mannose consumption rate as assumed to follow Michaelis-Menton kinetics:

$$q_M = \frac{V_M M}{K_M + M}$$

The maximum reaction rate is $V_M$ and the $K_M$ is the Michaelis-Menton constant. Data from cell culture plates suggested that the relative rate of production of high mannose species was proportional to the mannose concentration (FIG. 12(B)):

$$\frac{dH}{dP} = F_H M$$

Here H is the concentration of high mannose species and $F_H$ is the high mannose proportionality factor. Examination of previous data (not shown) suggested that $F_H$ varied with cell density so the following purely empirical equation was used for $F_H$:

$$F_H = K_1 * (K_2 + N)$$

$K_1$ and $K_2$ are empirical constants. Finally, the rate of change of high mannose is found via the chain rule:

$$\frac{dH}{dt} = \frac{dH}{dP}\frac{dP}{dt} = q_P K_1 (K_2 + N) M N$$

All the model parameters were determined via least squares regression of the training data shown in FIG. 14. The parameters were found by fitting the cell growth profile shown in FIG. 14(C). The value for $q_p$ was found by fitting the titer curve shown in FIG. 14(D). The decline in titer after day 12 is due to switching from an ultafiltration membrane (for which the sieving coefficient, S, is zero) to a microfiltration membrane (which gave a sieving coefficient in the range 0.76 to 0.78. The remaining parameters were found by fitting those equations to the data in FIG. 14(A) and FIG. 14(B) simultaneously.

The parameter values used in the model and their 95% confidence limits are shown in Table 4. Numerical values of model parameters and confidence limits obtained from training data and used for MPC. Graphs of the resulting model fit to the training data are shown in FIG. 14 (dashed lines A-D), while the fits with the growth parameters used for MPC are the dotted lines. The parameter fit for the mannose Michaelis Menton constant, $K_M$ is much larger than the concentrations used, so the mannose consumption kinetics were effectively first order. The training data and subsequent demonstration of MPC were performed under identical conditions with the exception of the mannose concentration which served as the control lever for high mannose.

TABLE 4

Numerical values of model parameters and confidence limits obtained from training data and used for MPC.

| Parameter | Value | 95% Confidence Interval | Units |
|---|---|---|---|
| μ | 0.7415 (0.7048) [1] | [0.67, 0.83] | 1/day |
| $N_M$ | 13.8 (14.2) [1] | [12.5, 15.1] | SCV/L |
| $q_p$ | 0.1705 | [0.167, 0.179] | g/SCV/day |
| $V_M$ | 102.5 | N/A [2] | g/L/day |
| $K_M$ | 1.47 × 10³ | N/A [2] | g/L |
| $V_M/K_M$ [2] | 0.695 | [0.062, 0.077] | 1/day |
| $K_1$ | 0.00332 | [0.0029, 0.0038] | L²/g/SCV |
| $K_2$ | 4.2 | [2.57, 5.84] | SCV/L |

Figure 15:
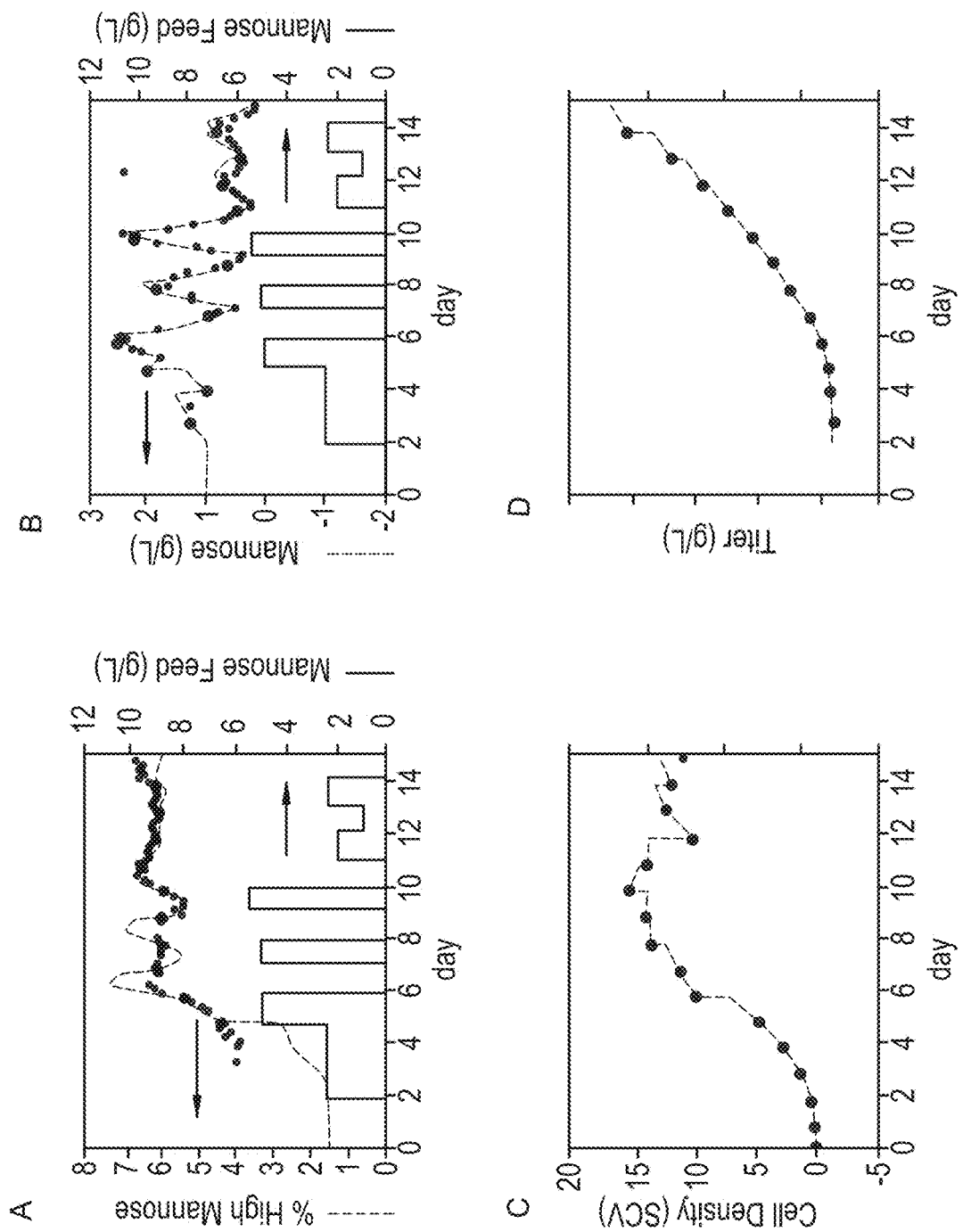
FIG. 15: Demonstration of control of % high mannose via Model Predictive Control. In all figures the symbols are measured values, but only the open symbols were used for the Model Predictive Control. The dotted line is the model output given the measurements and control action taken. The solid red lines in figures A and B show the mannose feed determined by MPC. A) % high mannose B) Reactor mannose concentration C) Cell density as arbitrarily scaled calculated volume (SCV) D) Product concentration
Figure 16:
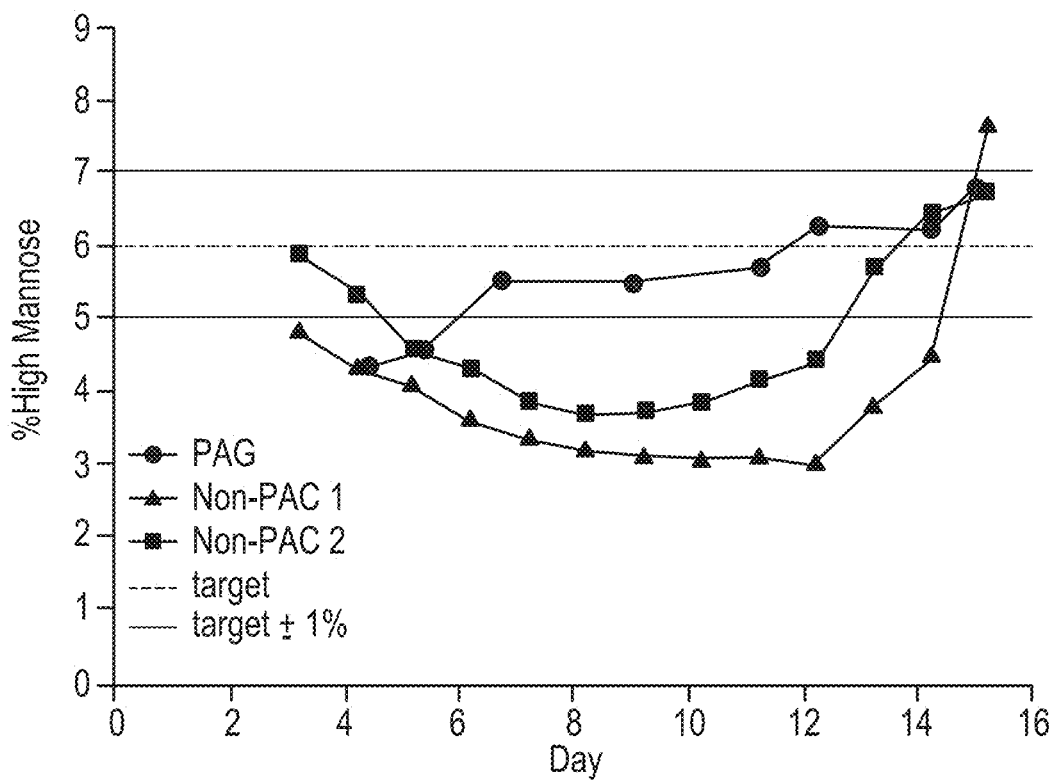
FIG. 16: Comparison of PAC and non-PAC data. The % high mannose data were obtained via the HILIC assay.

NOTE:
SCV is Scaled Cell Volume and is calculated from cell density and average diameter Demonstration of MPC to Control High Mannose Level Subsequent to derivation of the parameter values, the feed back loop was used in a bioreactor run to actively control the % high mannose level to 6%+/−1% for Antibody A Perfusion and mannose feeding were initiated on day 2 of the production culture. The initial mannose feed was set at a rate that would keep its concentration roughly constant in the reactor. This initial mannose feed rate was estimated based on previous experience with the process and was not part of the control loop. The control loop was started on day 5 of production. Samples were taken daily and analyzed to determine the inputs into the MPC model. The lag between reactor sample and rate change ranged between 5 and 14 hours, with an average of 8.5 hours. Once all the necessary data were available, they were manually input into the MATLAB model to calculate the next mannose feed rate. The resulting trajectory of the % high mannose, the other modeled quantities, and the resulting MPC based feed concentrations (calculated from feed rates) are shown in FIG. 15. Once control was initiated, the measured and modeled % high mannose rapidly increased and was maintained within 1% of the 6% target (FIG. 15(A)). The measured and modeled mannose concentration profiles rose and fell as expected in response to the mannose feed (FIG. 15(B)). The cell growth largely followed the assumed logistic curve with the exception of fairly significant deviations on days 6 and 12 (FIG. 15 (C)). The measured titer matched the model although the discontinuities in the last few days of culture are evidence that the model was under estimating protein production (FIG. 15(D)). The adjustment of the MPC model state to match measurements enabled good control of high mannose in spite of the observed deviations. In FIG. 16 a comparison between the PAC process and historical pilot plant runs is shown. The historical runs were performed using a conventional process which is similar in design and performance to the PAC process but without the active control loop. Instead, the conventional process is dependent on static process parameters to run within a margin of error for every batch to deliver the desired product, which will need to pass quality control for deposition. With the PAC process, PQ is measured near real time and, due to active control during the production run, will not require subsequent analytical characterization prior to disposition.

What is claimed is:

1. A method for harvesting a recombinant protein comprising
    establishing a cell culture by inoculating a bioreactor with mammalian cells expressing a recombinant protein,
    maintaining the cell culture by perfusing the cell culture with fresh cell culture media formulated or supplemented to achieve a concentration of at least 1 g/L of a non-ionic block copolymer and passing the cell culture through a hollow fiber filter having a pore size or molecular weight cut off that retains the recombinant protein in the bioreactor, and;

once a predetermined parameter is reached, perfusing the cell culture with fresh cell culture medium formulated or supplemented to achieve a concentration of at least 2, 3, 4, or 5 g/L of a non-ionic block copolymer and passing the cell culture through a hollow fiber filter having a pore size or molecular weight cut off that does not retain the recombinant protein in the bioreactor and collecting a permeate containing the recombinant protein, wherein the recombinant protein is denosumab.

2. The method of claim 1, wherein the non-ionic block copolymer is a polyoxypropylene-polyoxyethylene block copolymer.

3. The method of claim 1, wherein the non-ionic block copolymer is poloxamer 188.

4. The method of claim 1, further comprising a step of purifying the recombinant protein from the harvest permeate by one or more of flocculation, precipitation, centrifugation, depth filtration, affinity chromatography, size exclusion chromatography, ion exchange chromatography, mixed mode anion exchange chromatography, hydrophobic interaction chromatography or hydroxyapatite chromatography.

5. The method of claim 4, wherein purified denosumab is formulated into a pharmaceutically acceptable formulation.

* * * * *